(12) United States Patent
Ayers et al.

(10) Patent No.: US 6,645,233 B1
(45) Date of Patent: Nov. 11, 2003

(54) DRAINAGE TUBE WITH HEAT TRANSFER FUNCTION AND METHODS OF USE

(76) Inventors: Gregory M. Ayers, 1276 Nightingale Ct., Los Altos, CA (US) 94024; Scott M. Evans, 1252 Country Hills Dr., Santa Ana, CA (US) 92705

( * ) Notice: Subject to any disclaimer, the term of this patent is extended or adjusted under 35 U.S.C. 154(b) by 6 days.

(21) Appl. No.: 09/966,773

(22) Filed: Sep. 27, 2001

(51) Int. Cl.[7] .................................................. A61F 7/00
(52) U.S. Cl. ........................................ 607/105; 607/106
(58) Field of Search .............................. 607/105, 106, 607/98, 99, 100, 101, 102, 103, 104; 606/26, 29, 30, 31

(56) References Cited

U.S. PATENT DOCUMENTS 6,126,684 A * 10/2000 Gobin et al. ................ 607/113
6,299,599 B1 * 10/2001 Pham et al. ................ 304/113

* cited by examiner

*Primary Examiner*—Roy D. Gibson
*Assistant Examiner*—Aaron Roane
(74) *Attorney, Agent, or Firm*—Fulbright & Jaworski L.L.P.

(57) ABSTRACT

A drainage tube for controlling a patient's temperature and draining fluids from a patient's chest or other body cavity includes a generally tubular elongate body having one or more drainage lumens with one or more drainage ports disposed along the distal portion of the drainage tube. The drainage tube also comprises one or more flow lumens for transporting a heat exchange fluid to one or more heat exchange elements that exchange heat with tissue in the patient's chest or other body cavity. The drainage tube may have an internal heating element that heats or cools the heat exchange fluid. A heat exchange element may include an everting balloon that expands out of a cavity in the elongate body after intubation of the drainage tube. The expansion of the everting balloon may be assisted with a moveable inner shaft disposed in the elongate body.

10 Claims, 19 Drawing Sheets

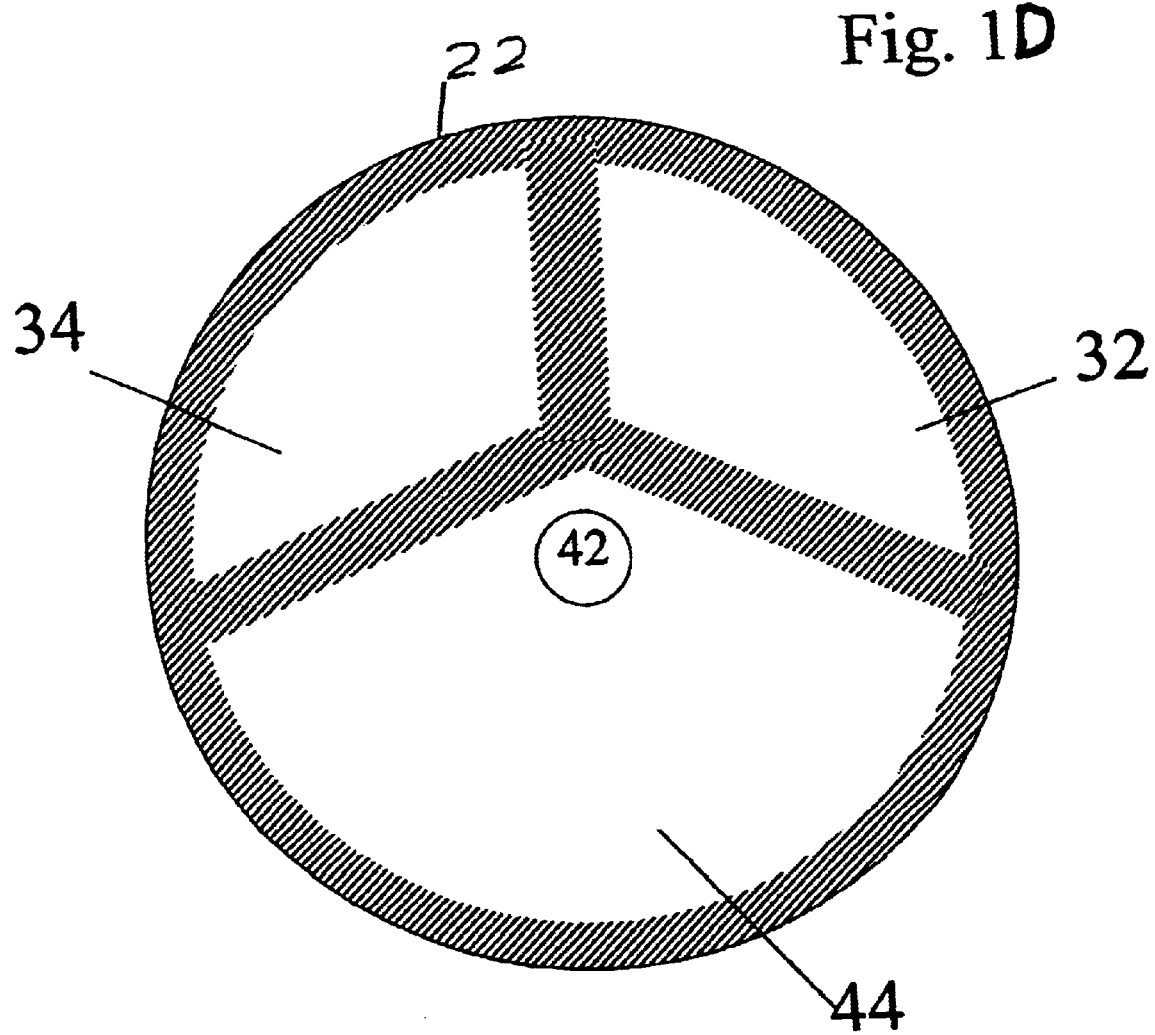

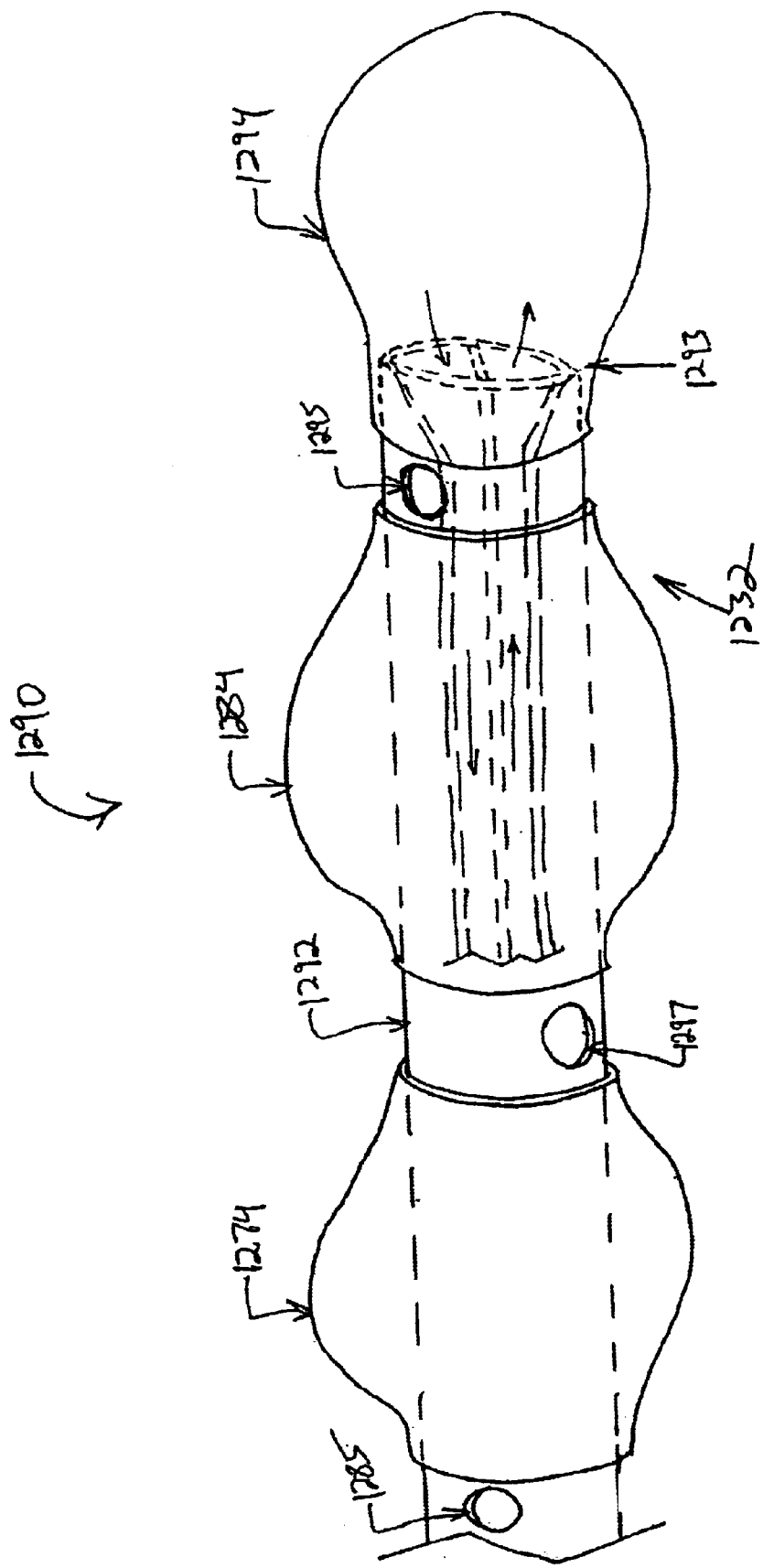

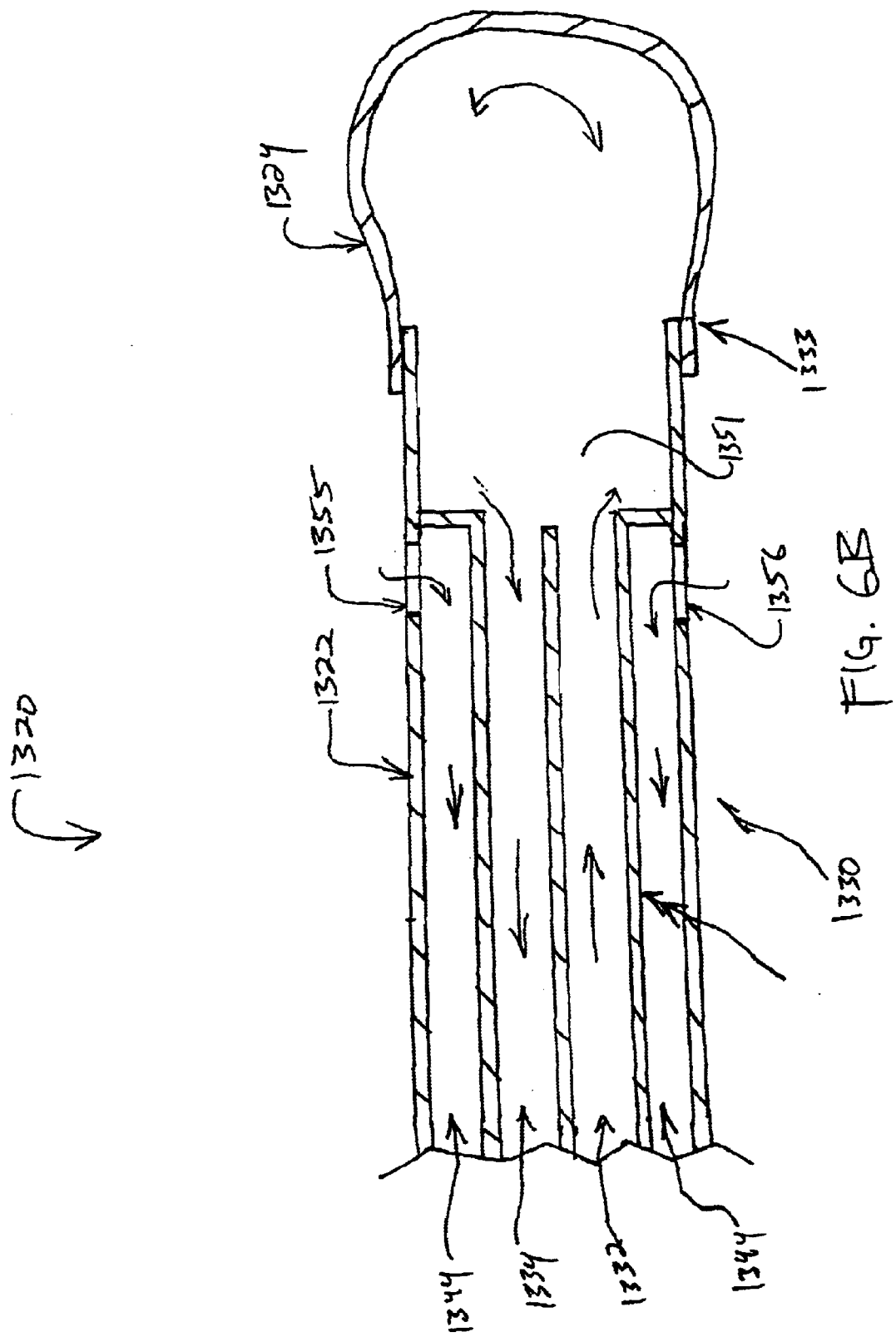

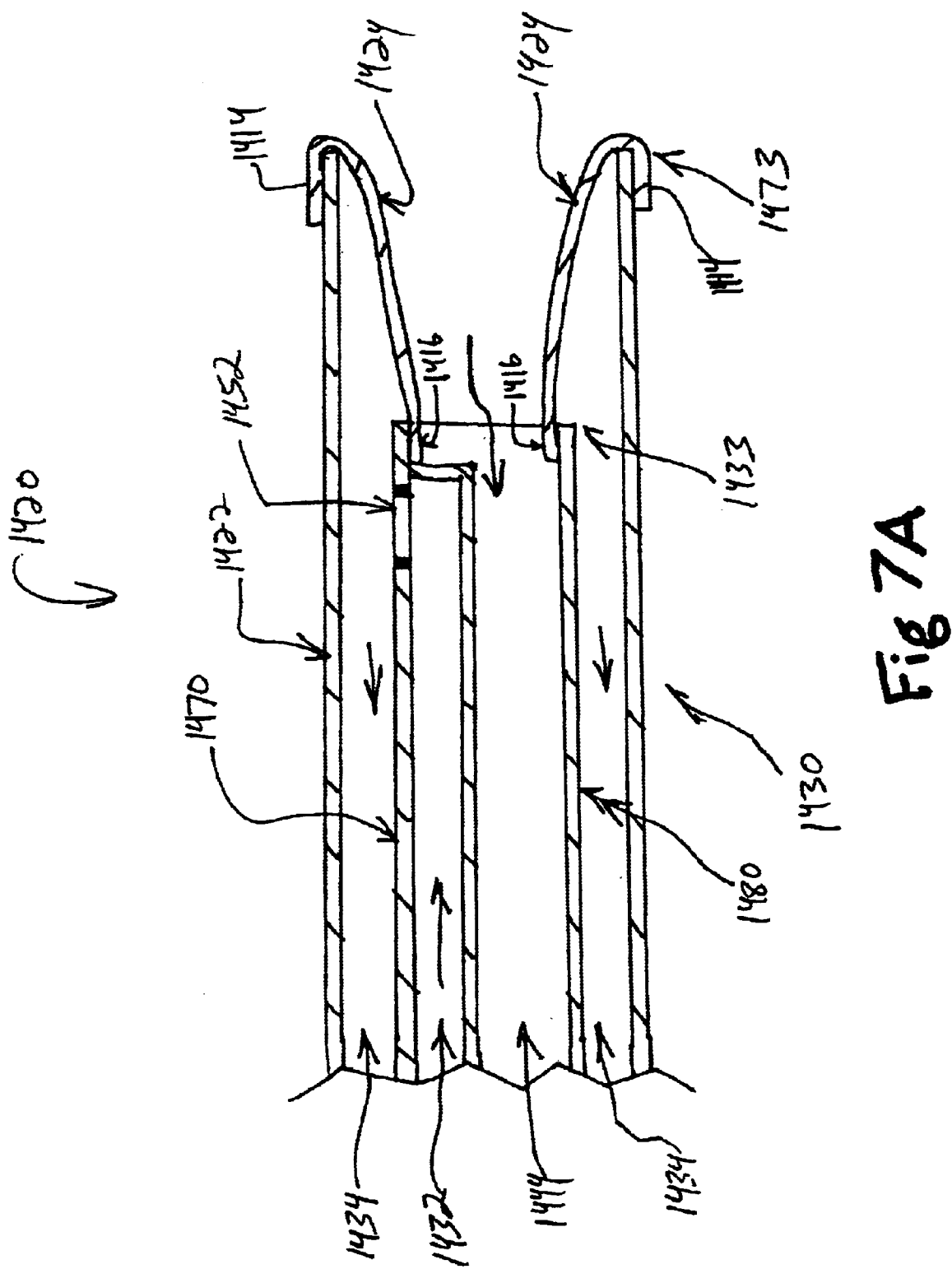

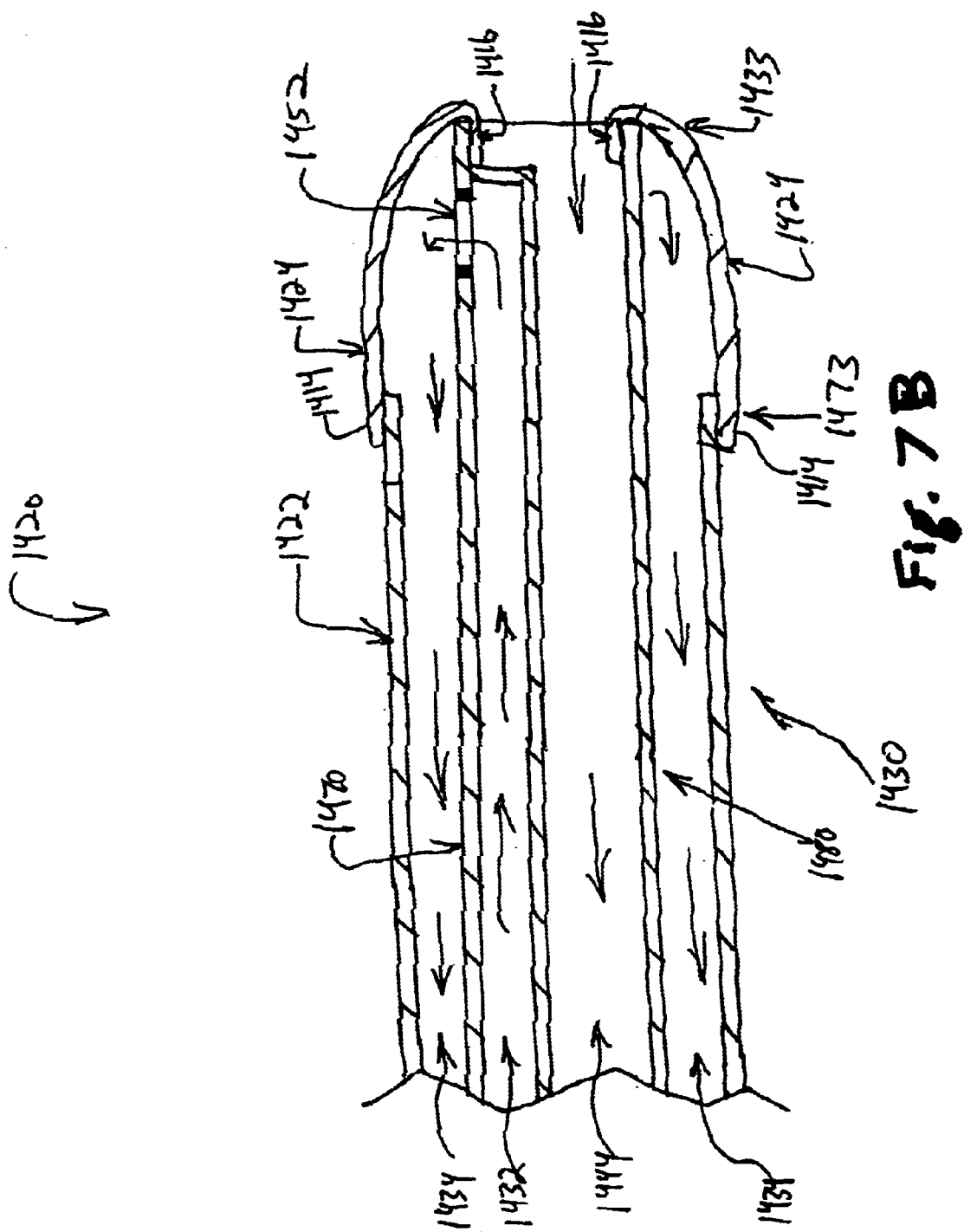

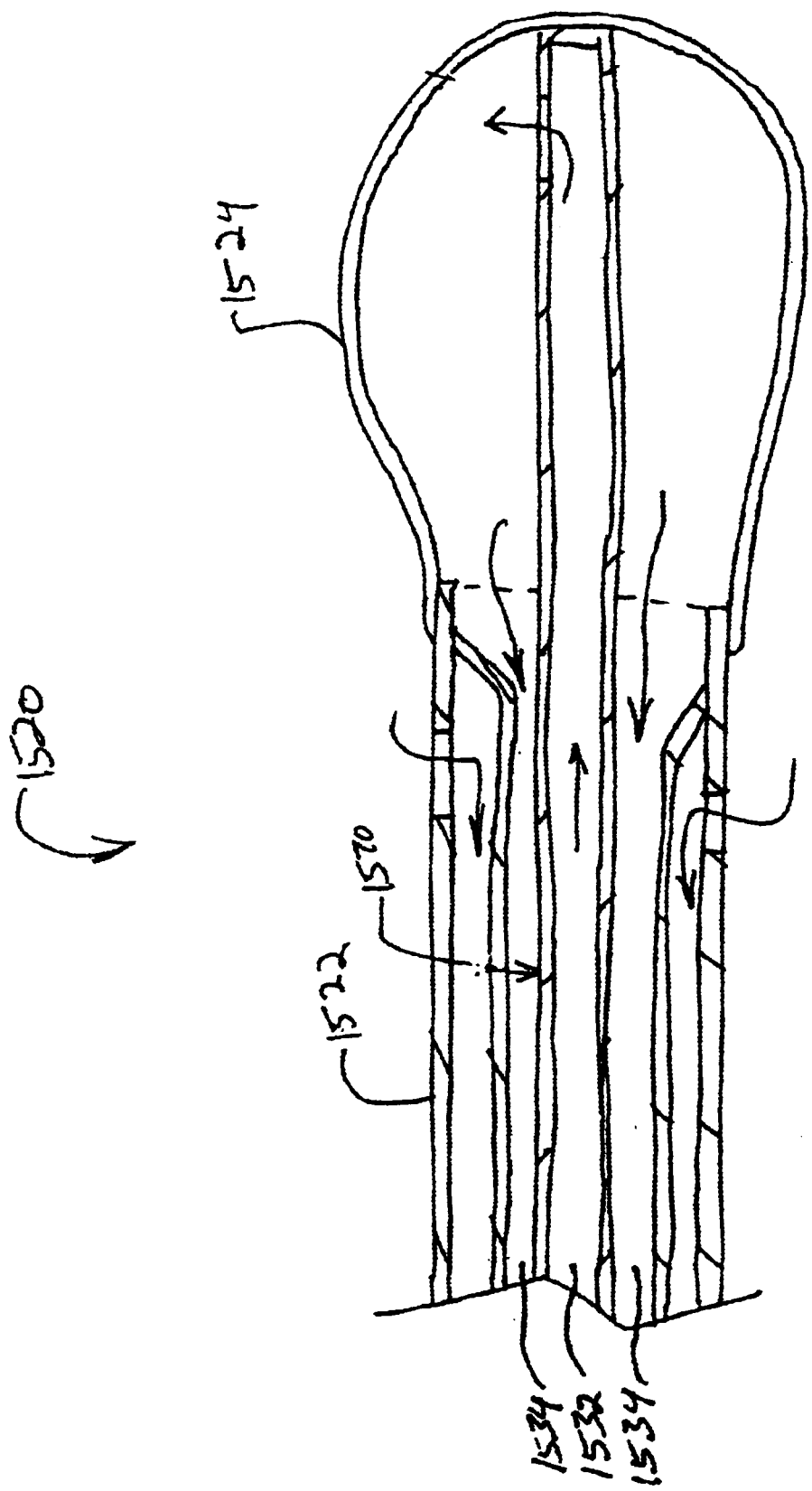

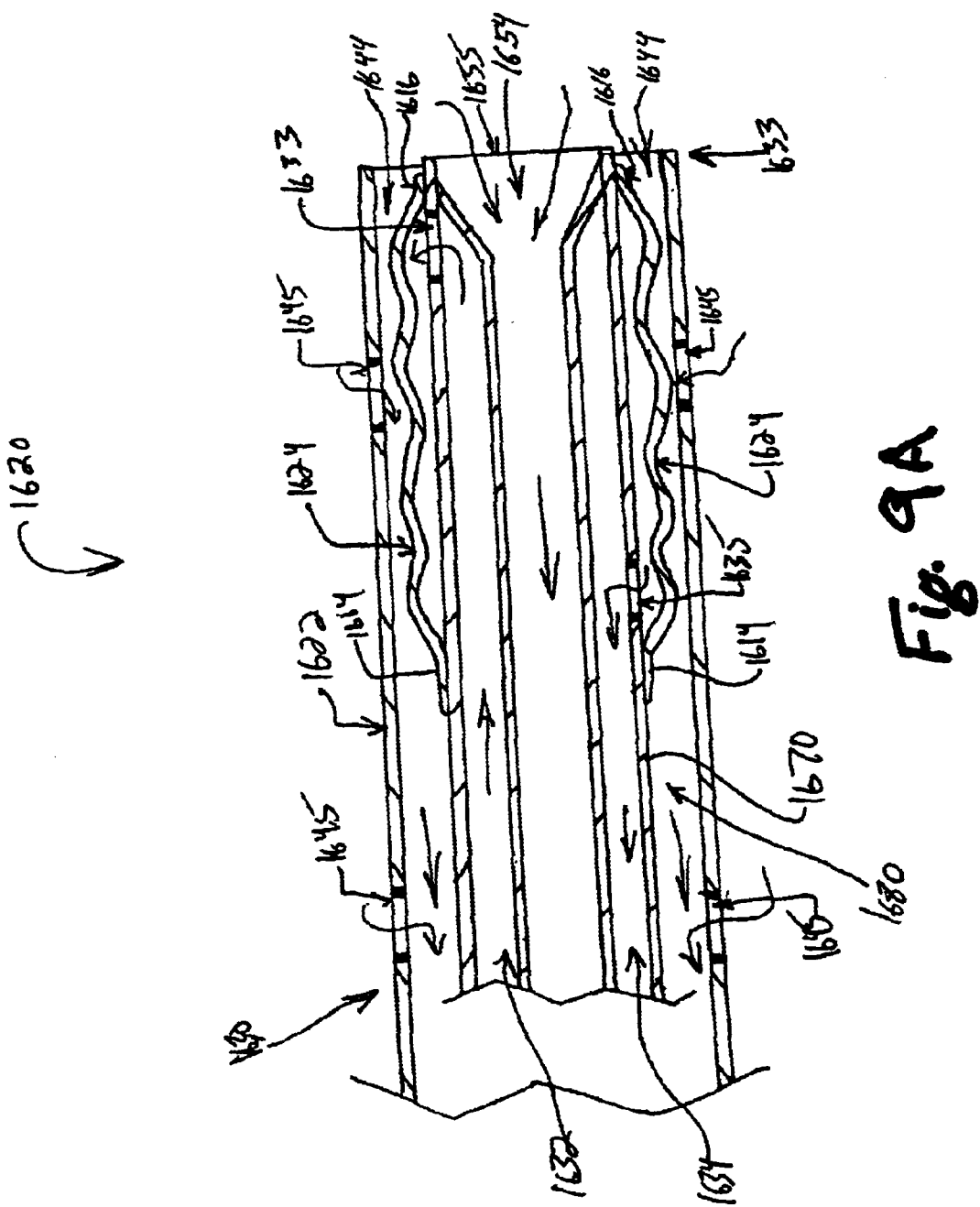

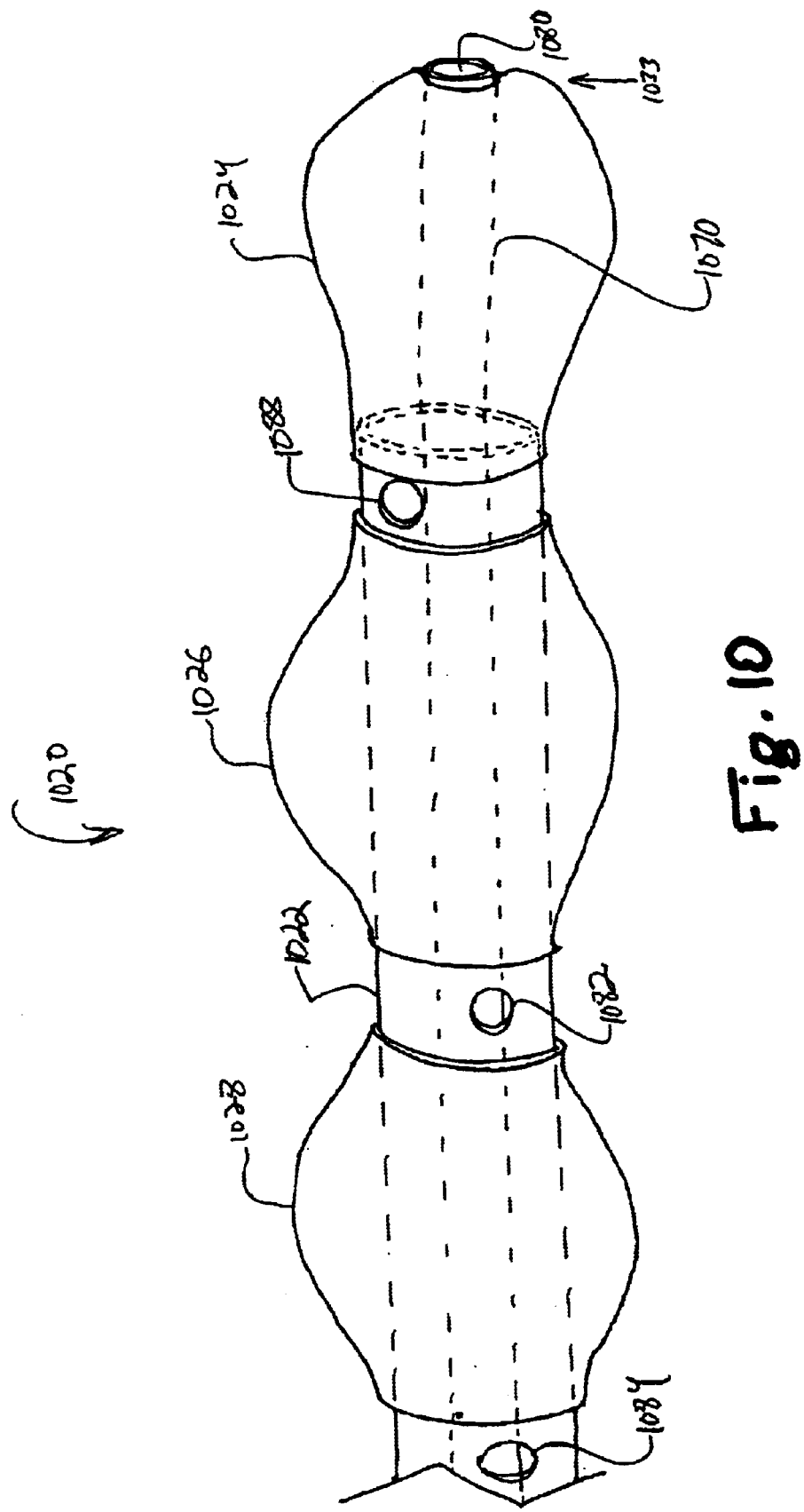

DRAINAGE TUBE WITH HEAT TRANSFER FUNCTION AND METHODS OF USE

BACKGROUND OF THE INVENTION

The field of the present invention is apparatus and methods for draining fluid from a body cavity of a patient.

Drainage tubes are typically used in many types of thoracic surgeries, especicially following cardiac surgery, and to treat cardiac or pulmonary conditions such as pneumothorax or pneumonia. Thoracic surgery may be performed on a patient for a variety of reasons, such as to remove a portion of a patient's lung, repair a patient's heart or the vessels of the lungs and heart, to operate on the esophagus, to determine whether a patient has lung or chest disease, or following injury to the lungs or the pleura, which is a membrane that covers the lungs. Such drainage tubes are distinct in medical usage from catheters inserted into passageways in the body, particularly as to size.

A drainage tube may be inserted through the skin and into the thoracic cavity of a patient. Typically, a tube is inserted through an intercostal space, which is the space between adjacent ribs. Once intubated in the patient, a tube may be used to drain fluids, including both gases such as air and liquids such as blood serum or pus, from the patient's thoracic cavity. Drainage may be carried out by suction with liquids and gases draining through the center lumen of the tube.

One specific application for drainage tubes is the treatment of conditions that can cause a patient's lung to collapse. Between the lungs and the membrane lining the chest wall is the pleural space. The pleural space facilitates breathing by having a vacuum created within the space as the volume increases with diaphragm and rib movement and forcing the lungs to expand. When the pleural space has been violated or cut into, such as during chest surgery, air rushes in and deflates or collapses the lungs. Air or other gases, as well as blood and other body fluids may enter the pleural space, destroying the ability of the space to make or maintain a vacuum normally maintained in the pleural space, and potentially causing the lung to collapse. To return the lung to normal size and function, air and fluids may be removed from the pleural space using a tube.

During or after surgery, in addition to using a tube to drain fluids (including liquids, air and other gases) from the patient's chest cavity, it may be desirable to reduce the patient's body temperature below normal body temperature so that the patient experiences hypothermia. Many advantages of hypothermia are known. By way of example, it has been found desirable to lower the temperature of body tissue in order to reduce the metabolism of the body. This has been particularly desirable in surgical applications where the reduced metabolism has made it possible to more easily accommodate lengthy operative procedures. In cases of stroke and several other pathological conditions, hypothermia also reduces the permeability of the blood/brain barrier. It inhibits release of damaging neurotransmitters and also inhibits calcium-mediated effects. Hypothermia also inhibits brain edema and lowers intracranial pressure. In other cases, it may be desireable to reduce the body temperature of a patient having a fever to a normal body temperature.

In yet other situations, it may be desirable to raise the patient's body temperature. Control of a patient's temperature may be problematic during hospital stays and particularly during active interventions such as thoracic surgery. The patient's body temperature may drift too low during surgery, potentially being detrimental to the patient's health. Body temperature often must be artificially maintained during surgery and post-operatively.

Conventional therapies used to manage patient temperature include acetaminophen (Tylenol), cooling blankets, heating blankets such as warm water blankets, forced warm or cool air, heat lamps, endovascular catheters, ice packs, ice baths, cold or warm infusions, ambient room cooling or warming, and cold saline rectal or gastric lavages. For some of the conventional therapies, the warming or cooling rates are restricted by the body's ability to resist surface cooling or heating with vasodilation and sweating. The conventional approaches to cooling a patient also may require additional steps, may require excessive time and do not provide for precise control of patient temperature over long periods of time. Further, some of these devices cover a significant portion of a patient's body, inhibiting access to the patient.

Other techniques for controlling patient temperature employ intravascular catheters that may be inserted into the patient's venous system. A fluid may be circulated through such catheters in a closed loop and exchange heat with blood flowing in the venous system, and may improve the patient's medical outcome. Such techniques may require that an additional incision be made so that the catheter may be advanced into the patient's venous system.

SUMMARY OF THE INVENTION

The present invention is directed to a drainage tube with a heat exchange function and methods for its use. A heat exchange element or elements is combined with a drainage lumen and one or more drainage ports to provide efficient temperature control of, drainage of and access to tissue in the patient's thoracic or other body cavity.

In a first separate aspect of the invention, a drainage tube comprises a heat exchange element that exchanges heat with tissue in the patient's thoracic or other body cavity, and a drainage lumen that communicates with tissue in the patient's thoracic or other body cavity through one or more drainage ports.

In a second separate aspect of the invention, a drainage tube comprises a heat exchange element that includes a balloon that extends distally from the distal end of the elongate body when operatively disposed.

In a third separate aspect of the invention, a drainage tube comprises a heat exchange element that includes an everting balloon that is at least partially contained in the elongate body during intubation of the drainage tube, the everting balloon extending distally from the distal end of the drainage tube when operatively disposed and inflated with heat exchange fluid.

In a fourth separate aspect of the invention, a drainage tube comprises a generally tubular elongate body defining an inflow lumen, an outflow lumen, and at least one drainage lumen. The inflow and outflow lumens circulate heat exchange fluid within one or more heat exchange elements connected with a distal, implantable portion of the drainage tube, while the drainage lumen provides a drainage channel for fluids (including gases) in the patient's thoracic or other body cavity.

In a fifth separate aspect of the invention, a drainage tube is provided with a drainage lumen that communicates with drainage ports that are disposed along the drainage tube at spaced intervals, such that the drainage tube may simultaneously drain fluids from different locations in the patient's thoracic or other body cavity, so as to increase the drainage rate and promote evenly distributed drainage.

In a sixth separate aspect of the invention, a drainage tube having a heat exchange function is provided with one or more infusion lumens, each infusion lumen having one or more infusion ports, the infusion ports being disposed along the drainage tube at spaced intervals, such that the drainage tube may be used to simultaneously introduce various infusion fluids into the patient at different locations in the patient's thoracic or other body cavity, so as to target different areas of the thoracic cavity or so as to more evenly distribute an infusion fluid throughout the thoracic or other body cavity.

In a seventh separate aspect of the invention, a heat exchange drainage tube is provided with multiple heat exchange balloons that are spaced along the distal portion of the elongate body to provide controlled and balanced heat transfer, with a gap between balloons to provide the drainage tube with flexibility.

In an eighth separate aspect of the invention, a heat exchange drainage tube is provided with multiple balloons have a gap between balloons, so that at least one drainage port may be disposed in the gap.

In a ninth separate aspect of the invention, a drainage tube comprises one or more heat exchange elements, a heating element, and a generally tubular elongate body defining a flow lumen and a drainage lumen. The flow lumen transports heat exchange fluid between one or more heat exchange elements connected with a distal, implantable portion of the drainage tube. The heating element is disposed on or in the distal portion of the drainage tube. The drainage lumen provides a drainage channel for fluids from the patient's thoracic or other body cavity.

In a tenth separate aspect of the present invention, it is contemplated that combinations of the foregoing separate aspects may be incorporated into a single embodiment.

Therefore, it is an object of the present invention to provide a drainage tube with a heat exchange function and methods for its use. Other and further objects and advantages will appear hereafter.

BRIEF DESCRIPTION OF THE DRAWINGS

FIG. 1D is a cross-sectional view of a fourth embodiment of a drainage tube;

FIG. 5 is a schematic side elevational view of a distal portion of a ninth embodiment of a drainage tube;

FIG. 6B is a schematic side sectional view of a distal portion of the drainage tube of FIG. 6A with the everting balloon in an operative configuration;

FIG. 7A is a schematic side sectional view of a distal portion of an eleventh embodiment of a drainage tube having an everting balloon in an insertion configuration and a moveable inner shaft in an insertion position;

FIG. 7B is a schematic side sectional view of a distal portion of the drainage tube of FIG. 7A with the everting balloon in an operative configuration and the moveable inner shaft in an operative position;

FIG. 8 is a schematic side sectional view of a distal portion of a twelfth embodiment of a drainage tube with an everting balloon in an operative configuration and a moveable inner shaft in an operative position;

FIG. 9A is a schematic side sectional view of a distal portion of a thirteenth embodiment of a drainage tube having a moveable inner shaft in an insertion position;

FIG. 10 is a schematic side elevational view of a distal portion of a fourteenth embodiment of a drainage tube having an inner shaft in an operative position.

DETAILED DESCRIPTION OF THE PREFERRED EMBODIMENTS

Figure 1:
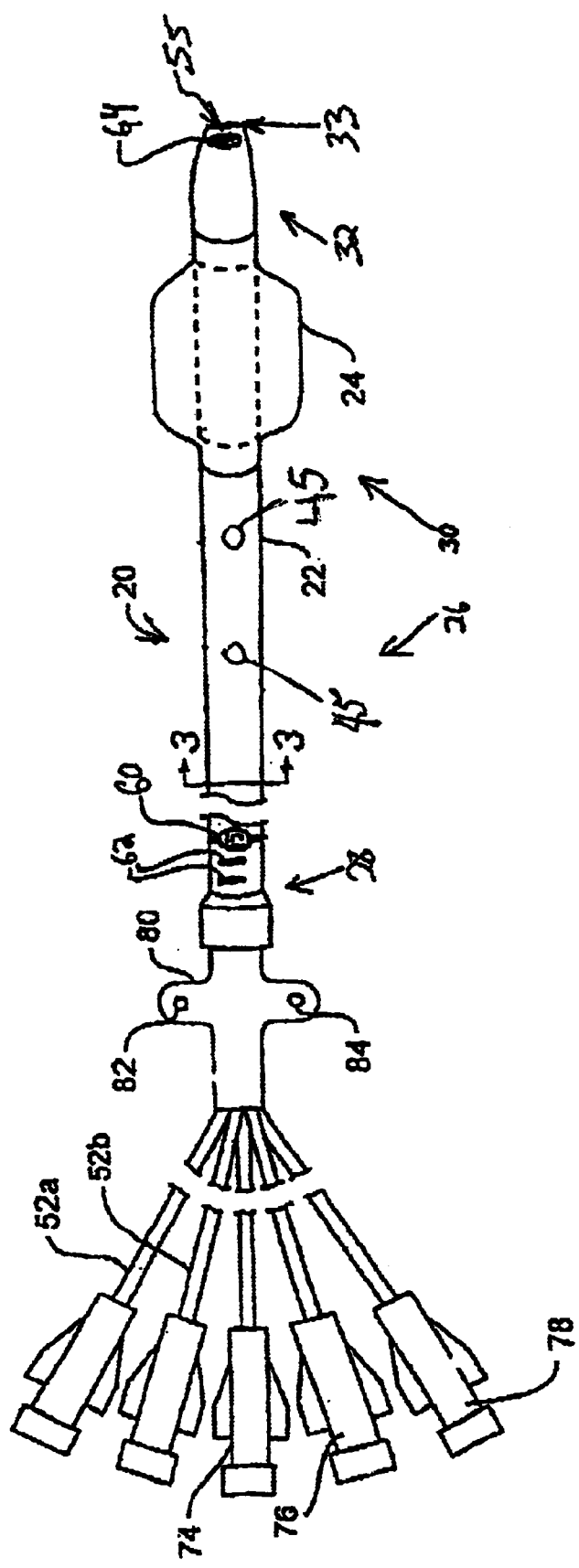
FIG. 1 is a schematic side elevational view of a first embodiment of a drainage tube.

The preferred embodiments will be described with reference to drawing figures, wherein like reference numerals are applied to like elements.

U.S. Pat. Nos. 6,146,411, 6,126,684, and 6,165,207 each of which is hereby incorporated by reference, disclose systems employing catheters that may be inserted into the body of a patient to exchange heat with the blood supply of the patient.

The present assignee has disclosed in U.S. Pat. No. 6,126,684 indwelling catheters that can be implanted in the body of a patient to exchange heat with the blood supply of the patient. The indwelling catheters of the above-referenced patent are disposed in a heat exchange relationship with the blood supply, and a coolant is circulated through the catheters in a closed loop. These catheters may change the temperature of body tissue and/or core body temperature, and may thereby improve the patient s medical outcome.

The heat exchange capability and other advantages of the heat exchange catheters disclosed in the above-referenced patents may be implemented with a drainage tube in the preferred embodiments here, so that a single device both accomplishes the functions of conventional body cavity drainage tubes and effectively manages patient temperature.

Figure 1A:
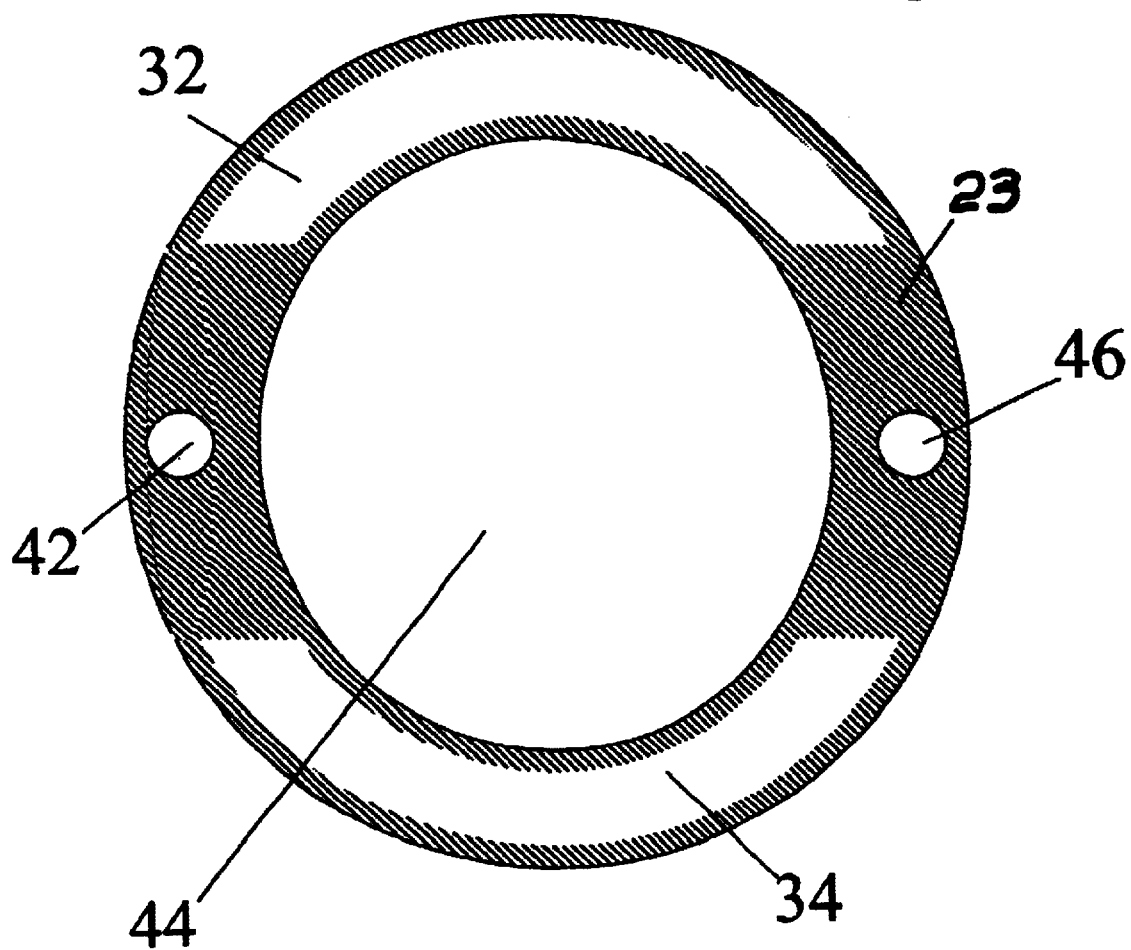
FIG. 1A is a cross-sectional view of the drainage tube of FIG. 1.

FIGS. 1 and 1A depict one embodiment of a drainage tube 20 adapted to exchange heat with a body tissue in a patient's thoracic, abdominal or other body cavity. The drainage tube 20 comprises an elongate body 22 having a substantially tubular configuration, having a proximal portion 26 with a proximal end 28, and having a distal portion 30 with a distal end 32.

In accordance with a preferred method, the drainage tube 20 may be inserted through a puncture or surgical incision in the patient's chest area, preferably between the patient's ribs or in the abdominal cavity. Following this initial introduction, the drainage tube 20 may be inserted into the space between the inner lining and the outer lining of the patient's lungs (the pleural space) or abdominal organs or peritoneal space. The relatively sizeable volume of the pleural space allows the use of one or more heat exchange elements 24 that have a relatively large volume and surface area to allow a relatively high rate of heat exchange.

The drainage tube 20 is preferably inserted into the pleural space adjacent one or more of the patient's lungs because the lungs are highly vascularized, allowing the heat exchange element 24 to transfer heat with a relatively large volume of blood flowing through the lung vasculature. In the case of open chest surgery, the drainage tube 20 may be positioned prior to closing the chest so that correct placement and operation may be confirmed.

When operatively disposed, the distal end 32 of the drainage tube 20 is disposed within the patient's thoracic cavity and the proximal end 28 is disposed outside of the patient's body, and the drainage tube 20 provides access to the patient's thoracic cavity and enables drainage of fluids from the cavity. The drainage tube 20 preferably exchanges heat with the patient's lungs, chest wall and other mediastinal organs which are highly vascularized, make up the body core, and allow efficient heat exchange with the patient's blood, and thereby with the rest of the patient's body.

The drainage tube may remain intubated in the patient until the blood, air or other fluid has drained from the chest and/or the patient's lung has re-expanded. The heat exchange relationship between the drainage tube and the thoracic cavity of the patient may be maintained for a prolonged duration—for example, from about one hour to about twenty-nine days. When the drainage tube is no longer needed, it may be removed by traction from outside the body.

One or more depth markings 60, 62 may be disposed on the elongate body 22 to indicate the length of a portion of the drainage tube 20 that is intubated into the patient. Preferably, the depth markings 60, 62 are disposed at least on the proximal portion 26 of the elongate body 22 so that they are visible when the drainage tube 20 is intubated into the patient. The markings 60, 62 preferably indicate a length of the drainage tube 20 measured from each marking 60, 62 to the distal tip 33 of the drainage tube 20 and may be disposed at spaced intervals, such as one-centimeter intervals. Each marking 60, 62 may comprise any symbol that may be understood to represent a length or relative length or degree of intubation. One marking 60 is shown to comprise a numeral indicative of length (in centimeters, for example) from the marking 60 to the distal tip 33 of the drainage tube. Other markings 62 may comprise dots, lines, hash marks, radiopaque bands that are detectable using X-rays, or other marks.

The elongate body 22 may also include a distal indicator 64 that indicates the position of the distal end 32 or distal tip 33 of the elongate body 22. The distal indicator 64 preferably is disposed near the distal tip 33 of the elongate body 22. The position of the distal indicator 64 inside the patient preferably may be determined using conventional medical technology, such as with X-rays or fluoroscopy. Information regarding the position of the distal end 32 or distal tip 33 of the elongate body 22 may aid proper placement of the drainage tube 20, so that the drainage tube 20 is inserted to a degree that optimizes the heat transfer rate without harming the patient.

The drainage tube 20 may further include an anchor configured for affixing the drainage tube 20 to the patient. The anchor may comprise a suture fitting 80. The suture fitting 80 can be made integrally with the drainage tube 20, or it can be made as a separate plastic fitting and engaged with the drainage tube 20. The suture fitting 80 includes two eyes 82, 84 through which sutures can be inserted and engaged with the patient or with a bandage or tape or other structure that is engaged with the patient's skin. An anchor may be especially desirable in cases in which the drainage tube is used for an extended period. Further, the drainage tube 20 may be resistant to inducing fibrosis. A hydrophilic coating may be applied to the drainage tube 20 to discourage the adhesion of body fluids or tissue to the tube 20.

Referring to FIG. 1A, which is a cross-sectional view of the drainage tube 20 of FIG. 1, the elongate body 22 comprises an inflow lumen 32, an outflow lumen 34, a drainage lumen 44, and two auxiliary lumens 42, 46. The various lumens 32, 34, 42, 44, 46 extend between the proximal portion and the distal portion of the elongate body 22.

Both the drainage lumen 44 and the auxiliary lumens 42, 46 may serve a multiplicity of functions, including drainage of fluids, infusion of drugs or fluids, irrigation, and accommodation of various sensors, such as thermistors to monitor the patient, thus generally providing access to the thoracic cavity as dictated by the particular application.

The drainage lumen 44 and the auxiliary lumens 42, 46 may also be configured to receive a guidewire, which is used to stiffen the drainage tube 20 during insertion of the drainage tube 20 into the patient and removed after insertion. Although this embodiment of the drainage tube 20 is shown with auxiliary lumens 42, 46, the drainage tube 20 need not include the auxiliary lumens 42, 46, or the drainage tube 20 may include additional auxiliary lumens (not shown), which may be suitable depending on the particular application.

In this embodiment, the drainage lumen 44 has a drainage port 55 at the distal end 33 of the elongate body 22 for providing communication between the drainage lumen 44 and the patient's thoracic cavity in which the drainage tube 20 may be intubated. Further, each auxiliary lumen 42, 46 preferably has a port providing communication between the auxiliary lumens 42, 46 and the patient's thoracic cavity.

The drainage tube 20 preferably is formed of a polymer material 23 that defines the various lumens 32, 34, 42, 44 and 46. A preferred material 23 is polyurethane, although other materials, such as nylon, polyethylene, PEBAX, PVC, Tygon® or the like can also be used. Considerations in selecting the appropriate material 23 include biocompatibility, flexibility, temperature change compatibility, and resistance to buckling.

At least one heat exchange element 24, such as a fluid-carrying inflatable balloon, is disposed near or on the implantable, distal portion of the elongate body 22. In this example, the heat exchange element 24 extends at least partially along the distal portion 30 of the elongate body 22. For ease of description, this embodiment is shown to have only one heat exchange element 24. The drainage tube may, however, have multiple heat exchange elements, as will be described below in connection with other embodiments.

In this embodiment, heat exchange fluid (not shown) flows within the drainage tube 20 to heat or cool a patient. The drainage tube 20 may be used to warm the peritoneal space, which may be desirable, for example, following abdominal surgery. The heat exchange fluid is remotely cooled or heated outside of the drainage tube 20, such as by a temperature control system (not shown) as described in U.S. Pat. Nos. 6,146,411 and 6,019,783, both of which are incorporated by reference herein. The heat exchange fluid is conveyed between the drainage tube 20 and, for example, a temperature control system, via an inlet tube 52a and an outlet tube 52b. External access to the drainage and auxiliary lumens 42, 44, 46 is supplied by lumen fittings 74, 76, 78.

The drainage lumen 44 typically would be connected through the drainage lumen fitting 74 with a drainage bag or reservoir. An external suction device that reduces the pressure in the drainage lumen 44 to encourage drainage of fluids through the drainage port 55 might also be connected with the drainage lumen 44 through the drainage lumen fitting 74.

Figure 1B:
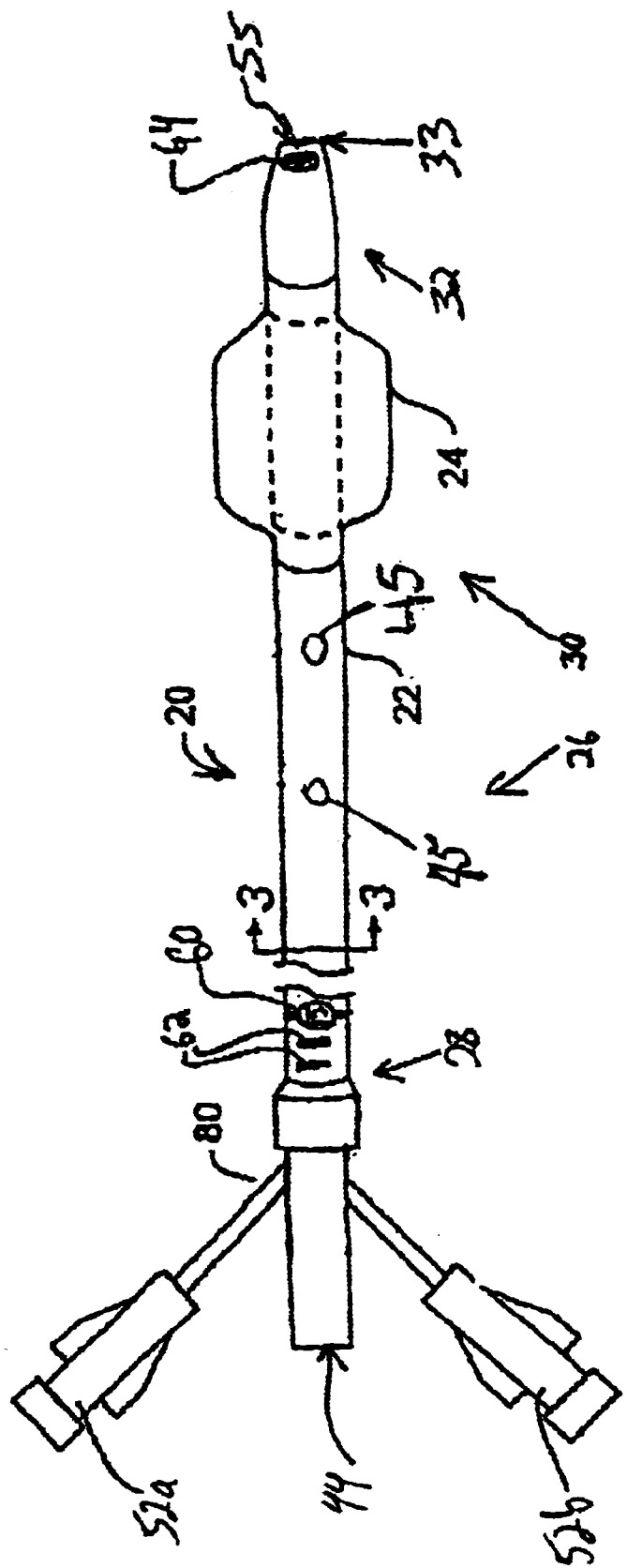
FIG. 1B is a schematic side elevational view of a second embodiment of a drainage tube.

FIG. 1B depicts another embodiment of the drainage tube 20. The elements shown in FIG. 1B correspond to the elements indicated by like numbers in FIG. 1 and are described in greater detail in connection with FIG. 1. This embodiment is depicted without the auxiliary lumens shown in FIG. 1A (42, 46 in FIG. 1A) or the suture fitting shown in FIG. 1 (80 in FIG. 1), but optionally may include these elements. Briefly described, heat exchange fluid may flow through an inlet tube 52a toward a heat exchange element 24, and flow away from the heat exchange element through an outlet tube 52b. Fluid may drain through the drainage ports 45, 55 and into drainage lumen 44.

Figure 1C:
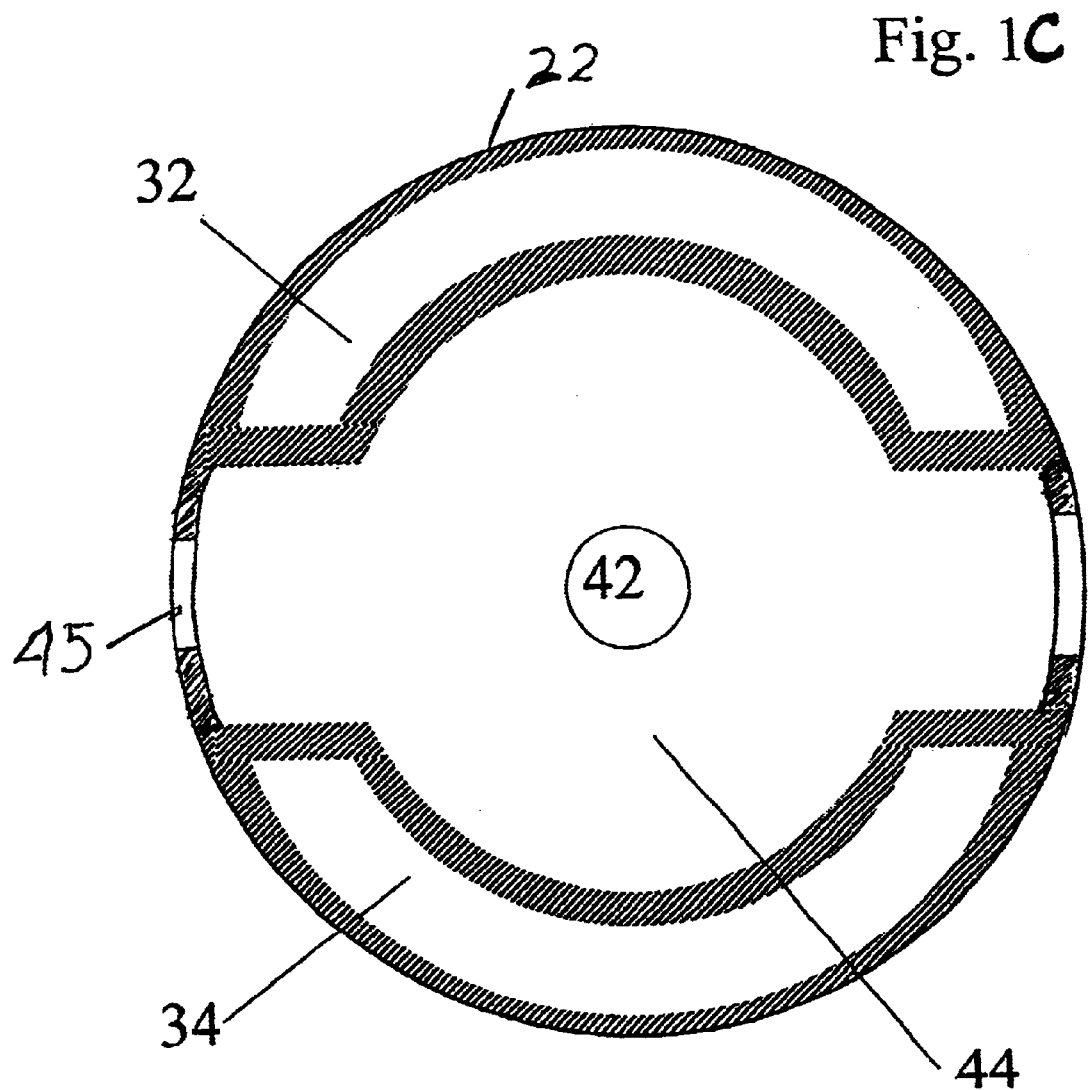
FIG. 1C is a cross-sectional view of a third embodiment of a drainage tube.
Figure 1E:
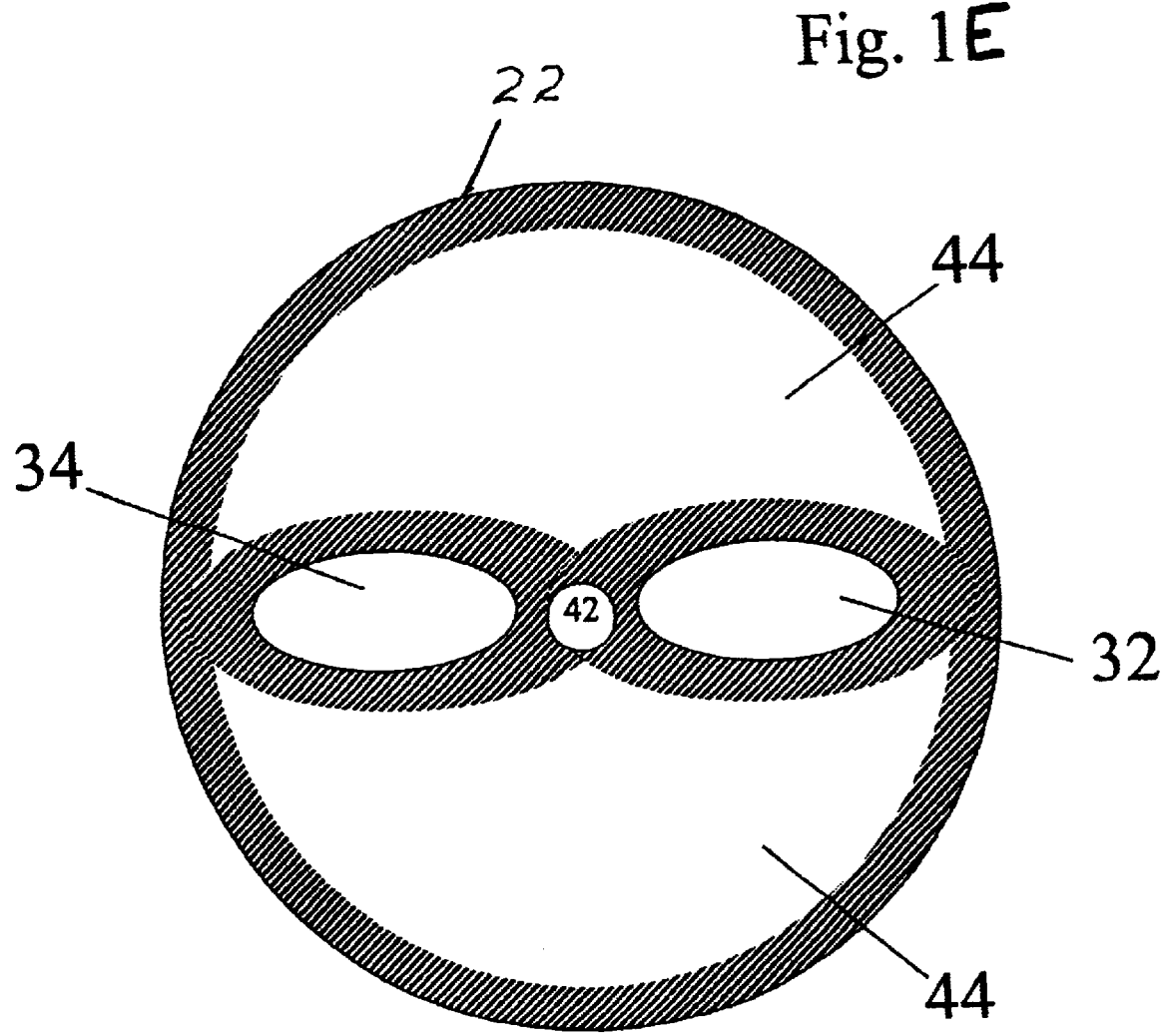
FIG. 1E is a cross-sectional view of a fifth embodiment of a drainage tube.

The various lumens may be arranged in a variety of configurations. Alternate cross-sectional configurations of drainage tubes are shown in FIGS. 1C, 1D, and 1E. The functions of the lumens 32, 34, 42, 44 shown in FIGS. 1C–E are similar to the functions of the lumens described in connection with FIG. 1A. The elongate body 22 comprises an inflow lumen 32, an outflow lumen 34, and a drainage lumen 44, and optionally may include one or more auxiliary lumens 42. Depending on the relative degrees of drainage and heat exchange desired, the drainage lumen 44 may be substantially larger in cross-section than the other lumens 32, 34, 44 as shown in FIGS. 1A, 1C, and 1E, or the drainage lumen 44 may be only somewhat larger than the inflow and outflow lumens 32, 34 as shown in FIG. 1D. As shown in FIGS. 1C, 1D, and 1E, the drainage lumen 44 may be disposed near the outer surface of the elongate body 22. As shown in FIG. 1C, ports 45 may be made in the longitudinal wall of the elongate body 22 to enable communication between the drainage lumen 44 and the outside surface of the drainage tube. Such ports 45 may permit drainage through the drainage lumen 44 along the length of the elongate body 22, in addition to any drainage provided through the tip of the elongate body 22.

Figure 2:
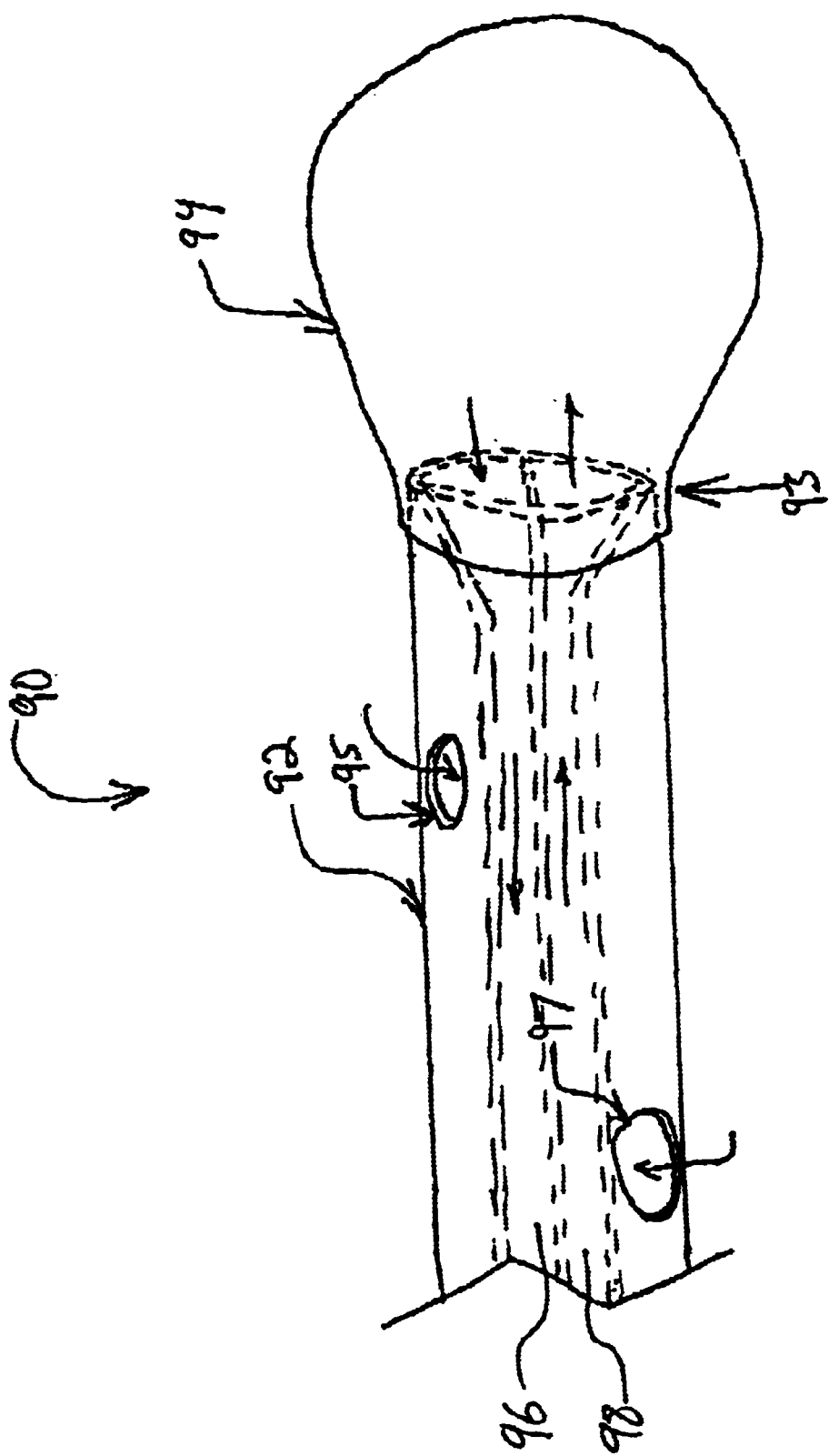
FIG. 2 is a schematic side elevational view of a distal portion of a sixth embodiment of a drainage tube.

The heat exchange element 24 of FIG. 1 is disposed along the distal portion 32 of the elongate body 22. Alternately, as shown in FIG. 2, a heat exchange element 94 may be disposed at and extend away from the distal end 93 of the elongate body 92. Drainage ports 95, 97 may be disposed proximally of the heat exchange element 94 on the exterior surface of the elongate body 92. The heat exchange element 94 may expand as it is filled with heat exchange fluid, contact tissue in the patient's thoracic cavity, such as one or more lungs, and exchange heat with the tissue. When the drainage tube 90 is to be removed from the patient, the heat exchange fluid may be drained from the heat exchange element 94 through the inflow lumen 98 and/or outflow lumen 96 so that the heat exchange element 94 deflates.

Figure 3:
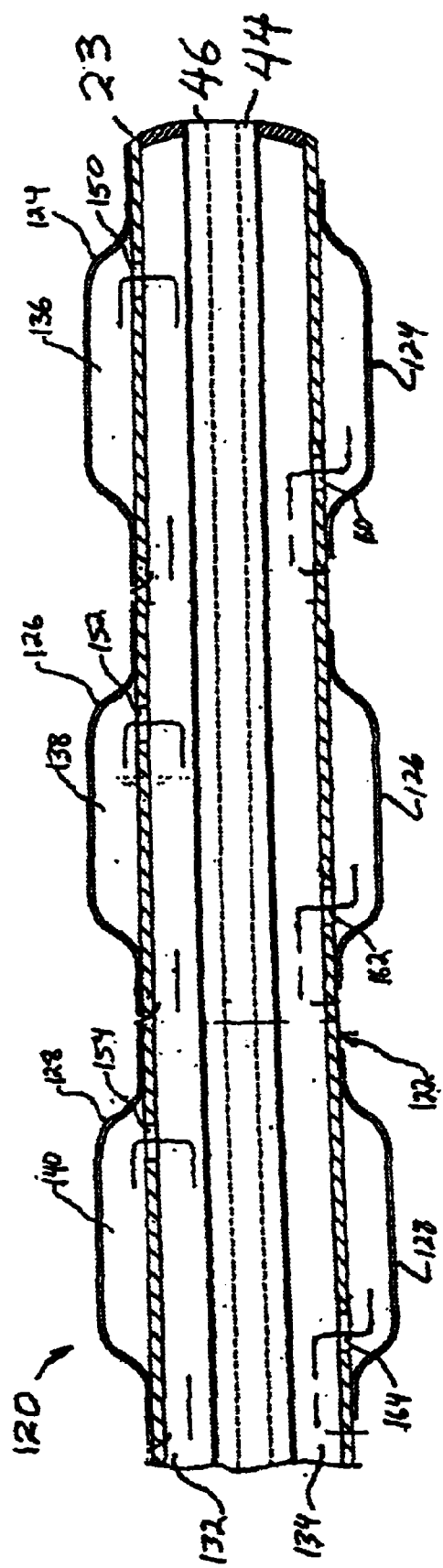
FIG. 3 is a schematic side sectional view of a distal portion of a seventh embodiment of a drainage tube.

FIG. 3 depicts a distal portion of a drainage tube 120 having three heat exchange elements 124, 126, 128. Although this embodiment has three heat exchange elements 124, 126, 128 disposed along the distal portion of the elongate body 122, a drainage tube may have a combination of various heat exchange elements described herein and heat exchange elements may be disposed at various locations on a drainage tube.

One of the advantages of employing multiple heat exchange elements is that the flow and temperature of heat exchange fluid that circulates in the drainage tube can be more easily controlled along the drainage tube such that a more even and balanced transfer of heat can be achieved. Further, multiple heat exchange elements may provide an increased surface area relative to embodiments having a single heat exchange element Another advantage may be increased ability of the drainage tube to bend and flex.

In this embodiment, each heat exchange element 124, 126, 128 defines with the elongate body 122 a cavity 136, 138, 140. Heat exchange fluid (as indicated by the arrows in FIG. 3) is circulated through the heat exchange elements 124, 126, 128, via the inflow lumen 132 and the outflow lumen 134.

The particular heat exchange fluid selected is preferably biocompatible to avoid harm to the patient in the event of inadvertent rupture. Candidate materials include sterile saline water and carbon dioxide gas, although other fluids having suitable viscosity, heat exchange and material compatibility characteristics can also be used.

The fluid may be either relatively cool or relatively warm, depending on whether patient cooling or heating is desired. While in each cavity 136, 138, 140 of each heat exchange element 124, 126, 128, the heat exchange fluid serves to provide a cold or warm fluid on an inner surface of each heat exchange element 124, 126, 128. Heat transfer occurs across the heat exchange element 124, 126, 128, effectively cooling or heating the tissue in the patient's thoracic or other body cavity. The temperature of the heat exchange fluid is remotely controlled in order to achieve a desired patient target temperature or temperature range.

The inflow lumen 132 serves as an inflow channel supplying the heat exchange elements 124, 126, 128 with heat exchange fluid which is circulated through the drainage tube 20, while the outflow lumen 134 serves as an outflow channel returning the heat exchange fluid from the heat exchange elements 124, 126, 128 toward the proximal portion of the drainage tube 120.

Each of the heat exchange elements 124, 126, 128, each of which preferably comprises a balloon, may be formed from a piece of flexible sheet material or extruded tubing formed into a molded balloon of the desired shape and size and then bound or otherwise fixed to the elongate body 122 to form each cavity 136 138 140. In one embodiment, each heat exchange element 124 126 128 is made of urethane, nylon, or PET and is thin-walled, i.e., has a wall thickness of less than three mils, and more preferably less than one and one-half mils.

The heat exchange elements 124, 126, 128 alternately may be made of metal such as steel, and may assume an appropriate configuration, such as an accordion-like configuration. Further, each heat exchange element 124, 126, 128 preferably is coated with an antimicrobial substance, as well as an anticlot substance, such as heparin.

Each balloon may be inflatable from a deflated configuration, wherein the balloon lies substantially flush with the elongate body 122, to an operational configuration, wherein the heat exchange fluid inflates each balloon outwardly from the elongate body 122. The flattened, deflated configuration facilitates insertion of the drainage tube 120 into the body of a patient.

Still referring to FIG. 3, the elongate body 122 includes an inflow port 150 152, 154 and an outflow port 160, 162, 164 for each heat exchange element 124 126 128. Each inflow port 150, 152, 154 is in communication with the inflow lumen 132. Each outflow port 160, 162, 164 is in communication with the outflow lumen 134. Heat exchange fluid introduced into the inflow lumen 132 enters each cavity 136, 138, 140 of each heat exchange element 124, 126, 128 through an inflow port 150 152 154, flows through the heat exchange element 124, 126, 128, exits the heat exchange element 124, 126, 128 through an outflow port 160, 162, 164, and flows through the outflow lumen 134 toward the proximal end of the drainage tube 120.

The amount of flow within each of the heat exchange elements 124, 126, 128 (which are preferably balloons in this case) may be controlled by the size of the inflow ports 150, 152, 154 and outflow ports 160, 162, 164. In this embodiment, this flow control is provided by the inflow ports 150, 152, 154. The outflow ports 160, 162, 164 are sized larger than their respective inflow ports 150, 152, 154 so that they offer little resistance to flow.

Further, the inflow ports 150, 152, 154 may be progressively smaller from the distal end to the proximal end. The inflow port 150 may be larger than the inflow port 152 which in turn may be larger than the inflow port 154. As a result, the resistance to the flow of heat exchange fluid in the most distal balloon is less than that in the most proximal balloon. This helps distribute the coolest or warmest heat exchange fluid equally among all of the balloons regardless of their positions along the elongate body 122. Further information regarding the positions and relative sizes of inflow ports and outflow ports is disclosed in U.S. Pat. No. 6,126,684, which is incorporated by reference herein.

In the embodiment depicted in FIG. 3, the heat exchange fluid flows in parallel flow paths, such that fluid circulating through one of the balloons returns to the proximal end of the drainage tube 120 without circulating through any other balloon. Using parallel flow paths, substantially equal heat exchange capacity is available in each balloon.

Figure 4:
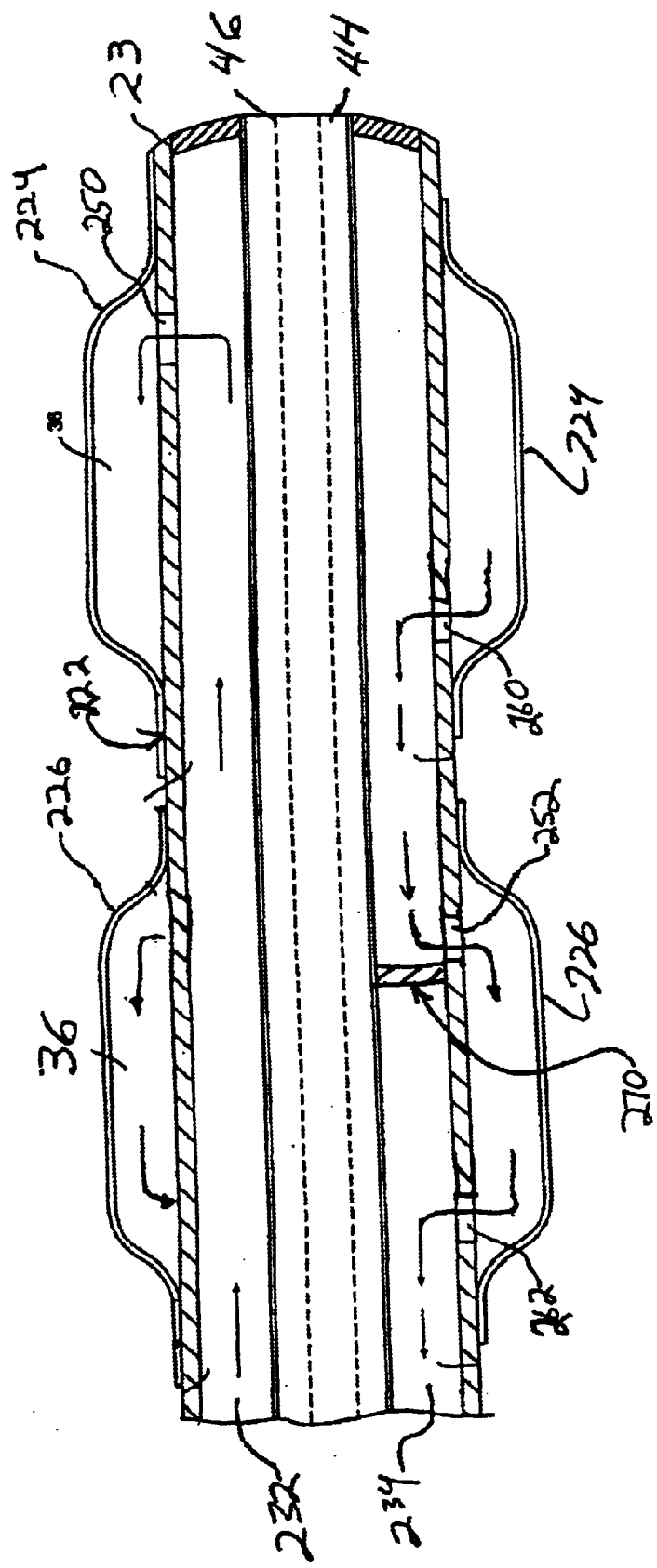
FIG. 4 is a schematic side sectional view of a distal portion of an eighth embodiment of a drainage tube.

In other embodiments, heat exchange fluid may flow in a serial flow path, such that fluid circulates through more than one balloon before returning to the proximal end of the drainage tube. An embodiment having a serial flow path is depicted in FIG. 4. Although FIG. 4 depicts an embodiment having two balloons, the principles set forth herein in connection with FIG. 4 may apply to drainage tubes having any number of balloons.

As shown in FIG. 4, a serial flow path may be provided by, for example, arranging the inflow ports 250, 252 such that only one inflow port 250 is in direct communication with the inflow lumen 232, and such that all other inflow ports 252 are in direct communication with the outflow lumen 234. Fluid flow through the outflow lumen 234 may be blocked by an obstruction 270 such that, for example, fluid flows into the outflow lumen 234 from a first balloon 224 through a first outflow port 260, flows in a proximal direction through the outflow lumen 234 toward a second inflow port 252, and flows through the second inflow port 252 into a second balloon 226. The obstruction 270 may direct fluid into the second inflow port 252 by blocking fluid flow through the outflow lumen 234 proximal of the second inflow port 252. Fluid flows through the second balloon 226 and into the outflow lumen 234 through the outflow port 262.

FIG. 5 depicts a drainage tube 1290 similar to the drainage tube of FIG. 2, with additional heat exchange elements 1284, 1274 disposed along the distal portion 1232 of the elongate body 1292. The drainage tube 1290 includes a heat exchange element 1294 extending distally from the distal end 1293 of the elongate body 1292. One or more drainage ports 1295 1297 1285 may be disposed on the distal portion 1232 of the elongate body 1292.

Figure 6A:
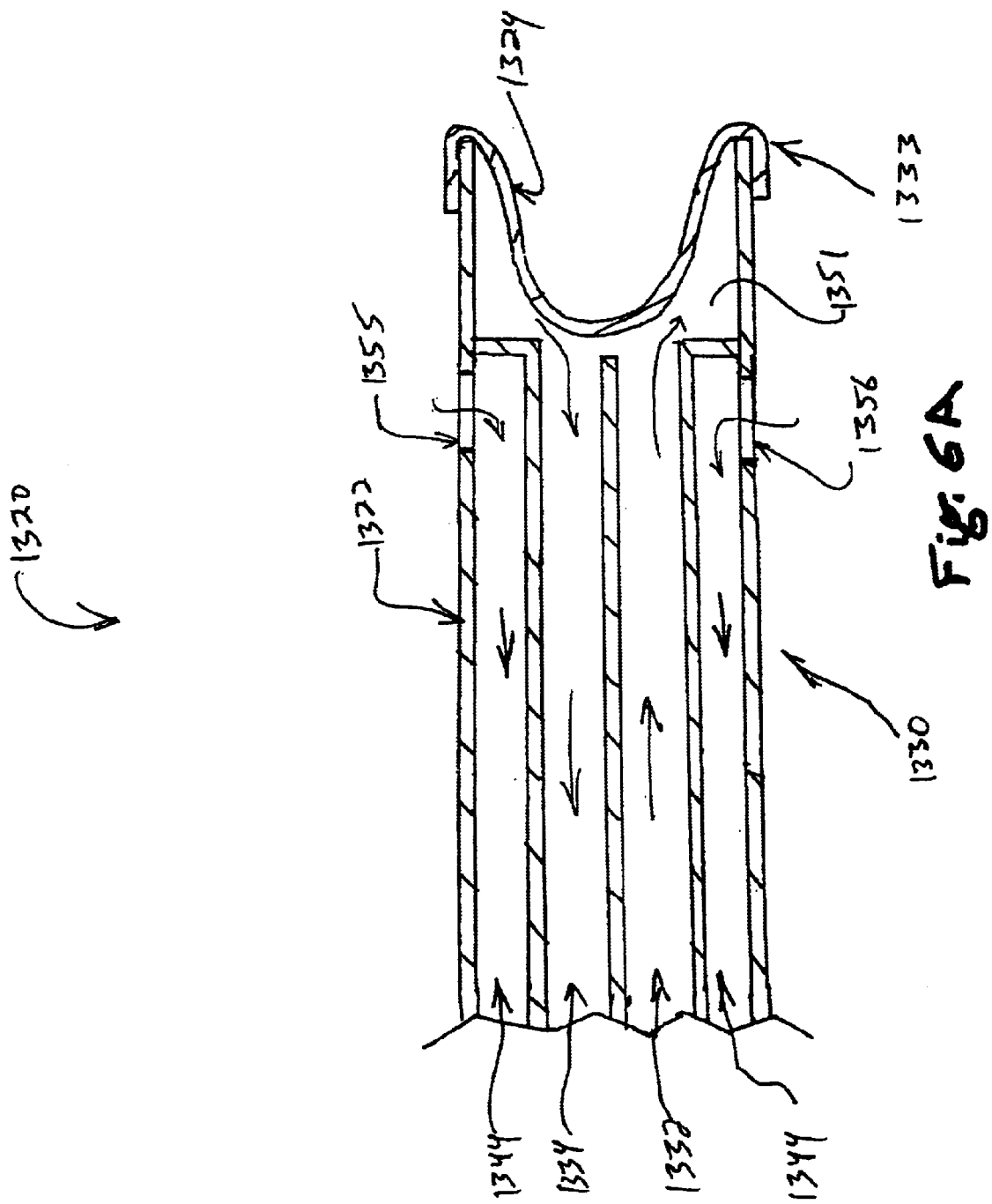
FIG. 6A is a schematic side sectional view of a distal portion of a tenth embodiment of a drainage tube having an everting balloon in an insertion configuration.

As shown in FIGS. 6A and 6B, a drainage tube 1320 may have a heat exchange element that includes an everting balloon 1324 that is moveable between an insertion configuration shown in FIG. 6A and an operative configuration shown in FIG. 6B. The everting balloon 1324 preferably sealingly engages the elongate body 1322 near the distal end 1333 of the elongate body 1322. The everting balloon 1324 may include bellows (not shown). Part of the distal portion 1330 of the elongate body preferably defines a cavity 1351 that the everting balloon 1324 may enter. In the insertion configuration, the everting balloon 1324 is at least partially contained inside the cavity 1351. Preferably, the distal portion 1330 of the drainage tube 1320 is intubated into the patient with the balloon 1324 in the insertion configuration shown in FIG. 6A. While in the insertion configuration, the balloon 1324 is contained so as not to inhibit intubation, and is at least partially protected against damage during the intubation process, which may involve relatively high forces on the distal portion 1330 of the drainage tube 1320.

Once the drainage tube 1320 is intubated, the balloon 1324 may be moved from the insertion configuration to the operative configuration shown in FIG. 6B. In this example, the balloon 1324 is moved by providing heat exchange fluid through the inflow lumen 1332 and into the balloon. As the heat exchange fluid enters the balloon 1324, the balloon 1324 expands, and everts (or turns at least partially inside-out) while being pushed out of the cavity 1351 in the elongate body 1322. To aid in expanding the balloon 1324 with heat exchange fluid, the outflow lumen 1334 may be blocked while heat exchange fluid flows into the inflow lumen 1332. In the operative configuration, the balloon 1324 preferably extends distally from the distal end 1333 of the elongate body 1322, and at least a substantial part of the everting balloon 1324 is outside of the elongate body 1322 so that the balloon 1324 may directly contact tissue in the patient's thoracic cavity.

In preparation for withdrawing the drainage tube 1320 from the patient, the balloon 1324 may be returned toward the insertion configuration shown in FIG. 6A to avoid damaging the balloon 1324 during withdrawal or inhibiting withdrawal. The balloon 1324 may be moved toward the insertion configuration by allowing heat exchange fluid to drain out of the balloon 1324. Pressure in the outflow lumen 1334 and/or inflow lumen 1332 may be decreased to draw the balloon 1324 into the cavity 1351 in the elongate body 1322, such as by applying suction to both of the inflow and outflow lumens 1332, 1334 or applying suction to either of the inflow or outflow lumens 1332, 1334 and blocking the other of the inflow or outflow lumens 1332, 1334.

Like the embodiment of FIG. 5, the drainage tube 1390 of FIGS. 6A and 6B may include one or more heat exchange elements (not shown) in addition to the everting balloon 1324. Preferably, the additional heat exchange elements would be located proximally of the everting balloon 1324 along at least part of the distal portion 1330 of the elongate body 1322.

In the embodiment of FIGS. 6A and 6B, pressure from the heat exchange fluid may move the everting balloon between the insertion and operative configurations. Alternately, as shown in FIGS. 7A and 7B, a moveable inner shaft 1470 may move or help move the everting balloon 1424 between an insertion configuration (shown in FIG. 7A) and an operative configuration (shown in FIG. 7B). In this embodiment, the inner shaft 1470 is substantially coaxial with the elongate body 1422, is positioned at least partially inside the elongate body 1422, and is moveable within the elongate body 1422. The inner shaft 1470 has a proximal shaft portion and a distal shaft portion 1480 with a distal shaft end 1433. Preferably, the inner shaft 1470 includes an inflow lumen 1432 or an outflow lumen, and an inflow port 1452 or an outflow port positioned on the distal shaft portion 1480 of the inner shaft 1470. Preferably, the inner shaft 1470 also includes a drainage lumen 1444, with a drainage port positioned at the distal shaft end 1433 of the inner shaft 1470.

The space between the inner shaft 1470 and the elongate body 1422 is shown as an outflow lumen 1434, but alternately may act as an inflow lumen. A drainage lumen (not shown) also may be defined in the space between the inner shaft 1470 and the elongate body 1422, with one or more drainage ports (not shown) disposed on the distal portion 1430 of the elongate body 1422.

In this example, a first portion 1414 of the everting balloon 1424 sealingly engages the distal portion 1430 of the elongate body 1422 near the distal end 1473 of the elongate body 1422, and a second portion 1416 of the everting balloon 1424 sealingly engages the distal shaft portion 1480 of the inner shaft 1470 near the distal shaft end 1433 of the inner shaft 1470.

The inner shaft 1470 is movable between an insertion position shown in FIG. 7A and an operative position shown in FIG. 7B. If the inner shaft 1470 moves, the everting balloon 1424 that is sealingly engaged to the shaft 1470 also moves. In the insertion position, the entire distal shaft portion 1480 of the inner shaft 1470 preferably is positioned within the elongate body 1422. When the shaft 1470 is in the insertion position, the everting balloon 1424 is in the insertion configuration, in which the balloon 1424 is at least partially contained inside the elongate body 1422.

In moving from the insertion position to the operative position, the inner shaft 1470 moves distally relative to the elongate body 1422. As the shaft 1470 is moved toward the operative position, it pushes at least part of the everting balloon 1424 outside of the elongate body 1422. The inner shaft 1470 preferably protrudes from the distal end 1473 of the elongate body 1422 in the operative position, and when the inner shaft 1470 is in the operative position, the everting balloon 1424 is in the operative configuration.

Alternately, as shown in FIG. 8, the everting balloon 1524 may not sealingly engage the inner shaft 1570. In this embodiment, the drainage tube 1520 has an inner shaft 1570 that may be pushed against the inside of the everting balloon 1524 to move the balloon 1524 toward the operative configuration shown in FIG. 8. Movement of the inner shaft 1570 toward the insertion position does not directly pull the balloon 1524 toward the insertion configuration (not shown). To move the balloon 1524 toward the insertion configuration, however, pressure in the inflow lumen 1532 or in the outflow lumen 1534 may be reduced, tending to deflate the balloon 1524 toward the insertion configuration.

Figure 9B:
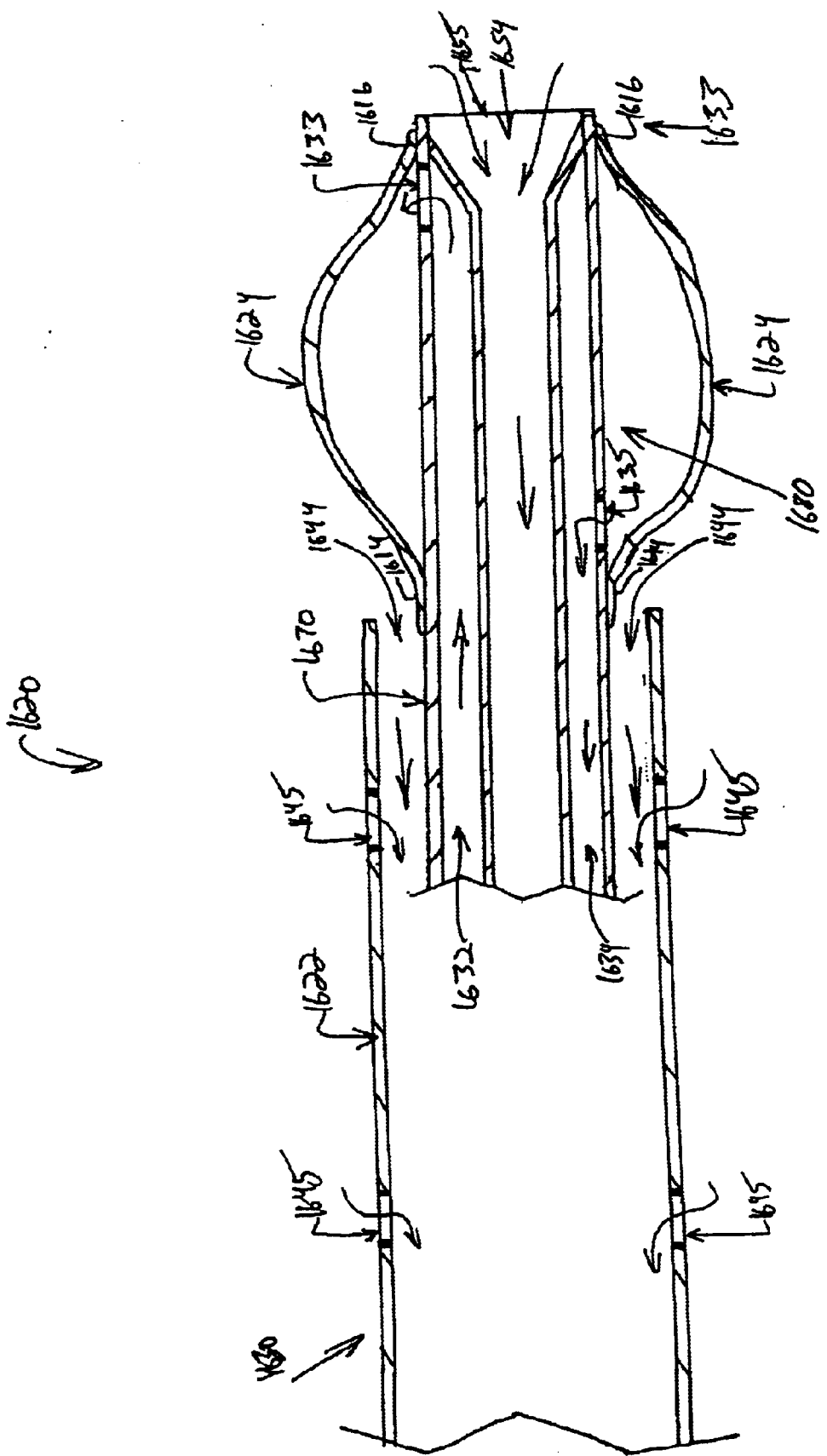
FIG. 9B is a schematic side sectional view of a distal portion of the drainage tube of FIG. 9A with the moveable inner shaft in an operative position.

As shown in FIGS. 9A (which depicts an insertion configuration) and 9B (depicting an operative configuration), both the first portion 1614 and the second portion 1616 of the everting balloon 1624 may sealingly engage the distal shaft portion 1680 of the inner shaft 1670. In this embodiment, the inner shaft 1670 preferably contains both the inflow lumen 1632 and the outflow lumen 1634, with the inflow port 1633 and the outflow port 1635 being disposed on the distal shaft portion 1680 of the inner shaft 1670. Preferably, a drainage lumen 1644 is disposed in the space between the elongate body 1622 and the inner shaft 1670, with one or more drainage ports 1645 disposed along the distal portion 1630 of the elongate body 1622. The inner shaft 1670 may also include a drainage lumen 1654, with one or more drainage ports 1655 disposed at the distal shaft end 1633 of the inner shaft 1670.

In drainage tubes having multiple heat exchange elements, the heat exchange elements are preferably spaced apart to define one or more gaps where the elongate body is exposed. Drainage ports may be located in gaps between heat exchange elements. For example, a drainage tube 1020 having three balloons 1024, 1026, 1028, as depicted in FIG. 10, may have a first drainage port 1080 disposed at a distal tip 1033 of the inner shaft 1070, may have a second drainage port 1088 disposed in a gap between two of the balloons 1024, 1026, may have a third drainage port 1082 disposed in a gap between two other of the balloons 1026, 1028, and/or may have a fourth drainage port 1084 disposed proximally of the balloon 1028. The drainage tube 1020 may have one, all, or any combination of the above-described drainage ports 1080, 1082, 1084, 1088, and may have drainage ports in other locations as well.

Providing multiple drainage ports that are spaced apart on a drainage tube allows, for example, the simultaneously drainage at different locations in the patient's thoracic cavity. Drainage at different locations may decrease the time needed to drain fluids from a particular location and allows drainage to continue even if some of the ports become blocked (such as by lying against tissue through which fluid does not drain). Additionally, the drainage tube 1020 may have an infusion lumen (not shown) and one or more infusion ports (not shown) spaced along the elongate body 1022.

The rate of heat transfer between the drainage tube and the patient depends on such factors as the volumetric flow rate of the heat exchange fluid and the temperature difference between the heat exchange element(s) and the tissue of the thoracic cavity. Other factors include the convection heat transfer coefficient of the two fluids involved in the heat exchange, the thermal conportivity and thickness of the barrier between the two fluids, and the residence time of the heat transfer. Increasing the cooling or heating rate may be accomplished by, for example, increasing the size (diameter and/or length) of the balloon, or increasing the temperature difference between the heat exchange fluid and the blood.

The size of the drainage tube is also restricted, the maximum size being dependent on the space available in the patient's thoracic cavity, space which may vary widely among different patients. A drainage tube that optimizes heat transfer for a larger patient may be too large for use in a smaller patient, and a drainage tube that optimizes heat transfer for a smaller patient may not optimize heat transfer in a larger patient. It is preferable, therefore, to size a drainage tube for the patient with which it will be used. For typical patients, a drainage tube may have an elongate body that is approximately 5 to 36 French in diameter, and more preferably 20 to 36 French in diameter. A drainage tube may have heat exchange elements that are approximately 2 to 8 centimeters in diameter, and more preferably 2 to 6 centimeters in diameter.

The length of each balloon also influences the heat transfer rate for each balloon. To optimize the heat transfer rate, the balloons preferably extend along substantially the entire length of the portion of the drainage tube that is intubated in the patient. Typically, this length is about 6 to 10 inches. The preferable length of each balloon will depend on the number of balloons used as well as the intubated length.

To optimize the heat transfer rate without deleterious physiological effects to the patient, the size of the patient's thoracic cavity may be measured prior to intubation, and a drainage tube size may be selected based on the size of the cavity.

The rate of heat transfer may also depend partially on the geometry of the heat exchange element. Because the operating temperature and size of a drainage tube are limited, the drainage tube geometry may take on increased importance to effectuate heat transfer. The flow of the heat exchange fluid inside the heat exchange elements may be non-laminar, such that much of the heat exchange occurs between only portions of the heat exchange fluid and tissue that is nearest the balloon surfaces. Mixing or disturbance of the flow path of the heat exchange fluid may increase the heat exchange rate.

The shape of the heat exchange element may be configured to promote mixing. Various balloon shapes may be employed in the embodiments, including but not limited to helical, cylindrical, fluted shapes, toroid, and tubular configurations. The particular shape selected depends on the application and the desired heat exchange and other characteristics. To promote mixing of the heat exchange fluid, a heat exchange element may be configured in helical shape, supplied with obstructions inside the heat exchange element that promote mixing, or otherwise configured, such that the flow of the heat exchange fluid is non-laminar, increasing the rate of heat transfer. Further information regarding mixing of the heat exchange fluid is disclosed in U.S. Pat. No. 6,126,684.

Although a heat exchange element may comprise a balloon, the heat exchange element alternately may have a different configuration, such as an array of flexible hollow fibers through which the heat exchange fluid is circulated. Further information regarding hollow fiber heat exchange elements and drainage tube systems having hollow fibers is disclosed in U.S. Pat. No. 6,165,207, which is hereby incorporated by reference as if fully set forth herein.

In many of the embodiments, a heat exchange fluid is heated or cooled outside of the drainage tube and circulates through one or more heat exchange elements. As shown in the drainage tube 1120 of FIG. 11, however, instead of circulating substantially continuously through each heat exchange element, the heat exchange fluid alternately may enter each heat exchange element 1124, 1126, 1128 and remain in each heat exchange element 1124, 1126, 1128 while being heated or cooled by a heating element 1110. The heating element 1110 may include a heating element, a wire or other conductive material, a refrigerant, or other material.

The heating element 1110 preferably is disposed near the heat exchange elements 1124, 1126, 1128 so that the heating element 1110 may efficiently exchange heat with the heat exchange fluid in the cavities 1136, 1138, 1140. Preferably, the heating element 1110 is embedded in or disposed along or near at least part of the distal portion 1130 of the elongate body 1122. In embodiments having a moveable inner shaft and a heat exchange elements attached to or disposed near the inner shaft, a heating element may also, or alternately, be embedded in or disposed along or near at least part of the distal shaft portion of the inner shaft.

A heat source (not shown) is used to heat or cool the heating element 1110. The heat source preferably is located externally of the drainage tube 1120 and is electrically, thermally or otherwise coupled with the heating element 1110. The heat source may include an electrical source, a heater, a refrigerator, a laser, a radio frequency (RF) energy source, a microwave energy source, an ultrasonic energy source, or other source of heat transfer.

Because the heat exchange fluid is not continuously circulating through the heat exchange elements 1124, 1126, 1128, separate inflow and outflow lumens are not needed. Instead, a single flow lumen 1132 may be employed to deliver heat exchange fluid through flow ports 1150, 1152, 1154 both to and from the cavities 1136, 1138, 1140 of the heat exchange elements 1124, 1126, 1128. A pump or gravity may be used to force heat exchange fluid into the heat exchange elements 1124, 1126, 1128. A pump, suction or gravity may be used to suck heat exchange fluid out of the heat exchange elements 1124, 1126, 1128. The structure and function of the flow lumen 1132 and flow ports 1150, 1152, 1154 are similar to that of the inflow lumens and ports and outflow lumens and ports described herein, except that the flow lumen 1132 and flow ports 1150, 1152, 1154 are used to transport heat exchange fluid both to and from the heat exchange elements 1124, 1126, 1128. The flow lumen 1132 extends between the proximal portion and the distal portion 1130 of the elongate body 1122. In embodiments having an inner shaft, a flow lumen may extend through the inner shaft.

In this example, a drainage lumen 1134 extends between the proximal portion and the distal portion 1130 of the elongate body 1122. Fluid may flow into the drainage lumen 1134 through each of various drainage ports 1185, 1187, 1189 disposed on the distal portion 1130 of the elongate body 1122. The drainage ports 1185, 1187, 1189 preferably are disposed adjacent to or between heat exchange elements 1124, 1126, 1128. Another drainage lumen 1141 may drain fluids through a drainage port 1143 located at the distal end 1133 of the elongate body 1122.

Figure 11:
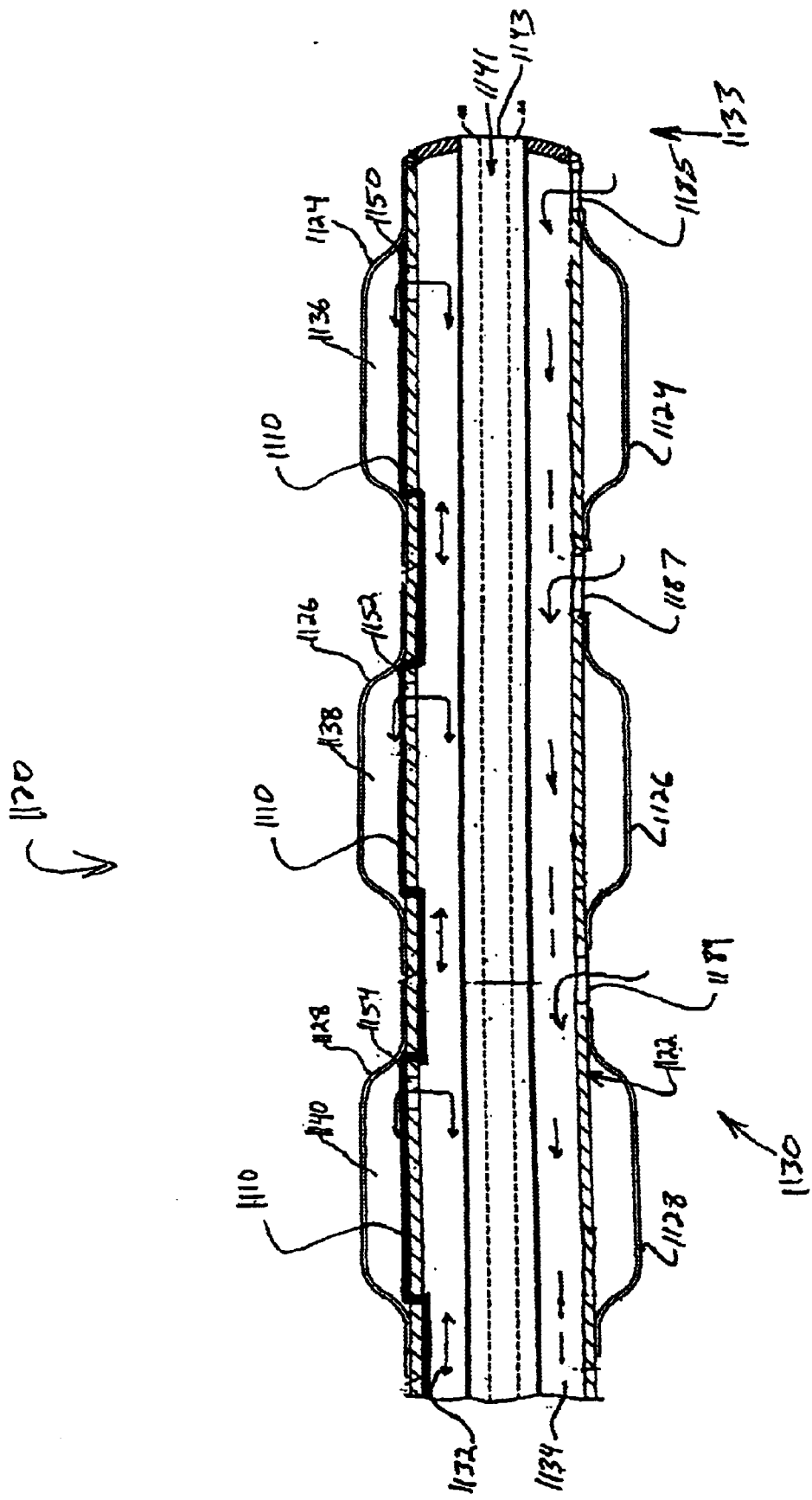
FIG. 11 is a schematic side sectional view of a distal portion of a fifteenth embodiment of a drainage tube having a heating element.

Alternately, the drainage tube 1120 of FIG. 11 may be configured without a heating element 1110. In such an embodiment (not shown), the heat exchange fluid may be heated or cooled outside of the drainage tube and pumped into one or more heat exchange elements. The heat exchange fluid may remain in the heat exchange element, exchanging heat with the patient's tissue, for some time (e.g., until the heat exchange fluid and adjacent tissue are nearly the same temperature), and then be pumped out of the heat exchange element(s). This process may then be repeated any number of times, the heat exchange fluid being re-heated or re-cooled outside of the drainage tube, and pumped back into the heat exchange element(s).

While the present invention has been described in terms of the preferred embodiments, other variations which are within the scope of the invention as defined in the claims will be apparent to those skilled in the art.

What is claimed is:

1. A method for controlling a temperature of a patient and draining a body fluid from the a body cavity of the patient, comprising
providing a drainage tube comprising an elongate body, at least one heat exchange element, at least one drainage lumen, and at least one drainage port;
placing at least one heat exchange element in a heat exchange relationship with tissue in the patient's cavity;
placing the drainage port in the patient's cavity;
providing heat transfer with the heat exchange element such that the heat exchange element is heated or cooled; and
draining a body fluid in the patient's cavity through the drainage port and drainage lumen;
measuring a dimension within the chest cavity; and
selecting the drainage tube having a size that is less than 100 percent of the measured dimension.

2. A method as set forth in claim 1, the step of draining a body fluid in the patient's cavity including the step of decreasing pressure in the drainage lumen.

3. A method as set forth in claim 1, the step of providing heat transfer with the heat exchange element including the step of circulating a heat exchange fluid through the at least one heat exchange element to effect heat transfer with the tissue in the cavity.

4. A method as set forth in claim 1, the step of providing heat transfer with the heat exchange element including the step of expanding one or more of the at least one heat exchange element with a heat exchange fluid.

5. A method as set forth in claim 1, the step of providing heat transfer with the heat exchange element including the step of changing a temperature of the heat exchange fluid with electric resistive heating, a laser, RF energy, microwave energy, ultrasonic energy or a heat sink.

6. A method as set forth in claim 1, the drainage tube further comprising at least one infusion lumen, the method further comprising infusing a fluid into the patient's cavity via the at least one infusion lumen.

7. A method as set forth in claim 1, further comprising expanding at least one heat exchange element to an inflated configuration to encourage maintenance of a space between the drainage port and body tissue defining the body cavity of the patient, such that blocking of the drainage port by the body tissue is inhibited.

8. A method for controlling a temperature of a patient and draining a body fluid from the a body cavity of the patient, comprising providing a drainage tube comprising an elongate body at least one heat exchange element, at least one drainage lumen and at least one drainage port;

placing at least one heat exchange element in a heat exchange relationship with tissue in the patient's cavity;

placing the drainage port in the patient's cavity;

providing heat transfer with the heat exchange element such that the heat exchange element is heated or cooled; and draining a body fluid in the patient's cavity through the drainage port and drainage lumen, the step of placing the at least one heat exchange element in a heat exchange relationship with tissue in the patient's cavity including the step of moving a heat exchange element from a position at least substantially inside the elongate body to a position at least substantially outside of the elongate body.

9. A method as set forth in claim 8, the step of moving the at least one heat exchange element including the step of inflating the at least one heat exchange element with a heat exchange fluid.

10. A method as set forth in claim 8, the drainage tube further comprising an inner shaft disposed at least partially inside and moveable within the elongate body and the step of moving a heat exchange element including the step of moving the inner shaft distally relative to the elongate body.

* * * * *